(12) United States Patent
Dobrinsky et al.

(10) Patent No.: US 12,171,535 B2
(45) Date of Patent: Dec. 24, 2024

(54) FLUORESCENT SENSING FOR EVALUATING FLUID

(71) Applicant: Sensor Electronic Technology, Inc., Columbia, SC (US)

(72) Inventors: Alexander Dobrinsky, Vienna, VA (US); Michael Shur, Vienna, VA (US)

(73) Assignee: Sensor Electronic Technology, Inc., Columbia, SC (US)

( * ) Notice: Subject to any disclaimer, the term of this patent is extended or adjusted under 35 U.S.C. 154(b) by 487 days.

(21) Appl. No.: 17/372,933

(22) Filed: Jul. 12, 2021

(65) Prior Publication Data

US 2021/0338091 A1    Nov. 4, 2021

Related U.S. Application Data

(63) Continuation of application No. 15/829,323, filed on Dec. 1, 2017, now Pat. No. 11,058,312.

(60) Provisional application No. 62/429,137, filed on Dec. 2, 2016.

(51) Int. Cl.
| | |
|---|---|
| *A61B 5/026* | (2006.01) |
| *A61B 5/00* | (2006.01) |
| *A61B 5/0275* | (2006.01) |
| *G01N 21/64* | (2006.01) |
| *G01N 33/58* | (2006.01) |
| *A61B 5/15* | (2006.01) |

(Continued)

(52) U.S. Cl.
CPC .......... *A61B 5/0261* (2013.01); *A61B 5/0071* (2013.01); *A61B 5/0275* (2013.01); *G01N 21/6428* (2013.01); *G01N 33/582* (2013.01); *A61B 5/15* (2013.01); *A61B 5/157* (2013.01); *A61B 8/06* (2013.01)

(58) Field of Classification Search
CPC ................ A61B 5/0071; A61B 5/0261; A61B 5/0275; A61B 5/15; A61B 5/157; A61B 8/06; G01N 21/6428; G01N 33/582
See application file for complete search history.

(56) References Cited

U.S. PATENT DOCUMENTS

2004/0208825 A1* 10/2004 Carpenter ................ B82Y 5/00
                                                               424/9.6
2008/0255403 A1* 10/2008 Voegele ................ A61B 1/043
                                                               977/904

(Continued)

FOREIGN PATENT DOCUMENTS

WO     2016154286 A1    9/2016

OTHER PUBLICATIONS

Wecker, Jennfier, U.S. Appl. No. 15/829,323, Notice of Allowance, May 10, 2021, 12 pages.

*Primary Examiner* — Jennifer Wecker
(74) *Attorney, Agent, or Firm* — LaBatt, LLC

(57) ABSTRACT

Approaches for evaluating fluid based on fluorescent sensing is disclosed. In one approach, a nanoparticle injector is configured to inject nanoparticles into a fluid. A detector is configured to determine a presence of the nanoparticles in the fluid. The detector can include a radiation source configured to irradiate the fluid with a target radiation and a fluorescent meter configured to measure an amount of fluorescence emitted from the fluid irradiated with the radiation. A control unit is configured to determine the a set of attributes corresponding to the fluid as a function of the measured amount of fluorescence.

20 Claims, 9 Drawing Sheets

(51) Int. Cl.
*A61B 5/157* (2006.01)
*A61B 8/06* (2006.01)

(56) References Cited

U.S. PATENT DOCUMENTS

| | | | |
|---|---|---|---|
| 2013/0266479 A1* | 10/2013 | Peterman | G01N 21/658 |
| | | | 422/69 |
| 2015/0125941 A1* | 5/2015 | Hirase | G01N 33/54326 |
| | | | 422/400 |
| 2015/0283265 A1 | 10/2015 | Peyman | |
| 2016/0299134 A1* | 10/2016 | Denomme | G01N 21/554 |
| 2018/0113068 A1* | 4/2018 | Weber | G01N 21/59 |

* cited by examiner

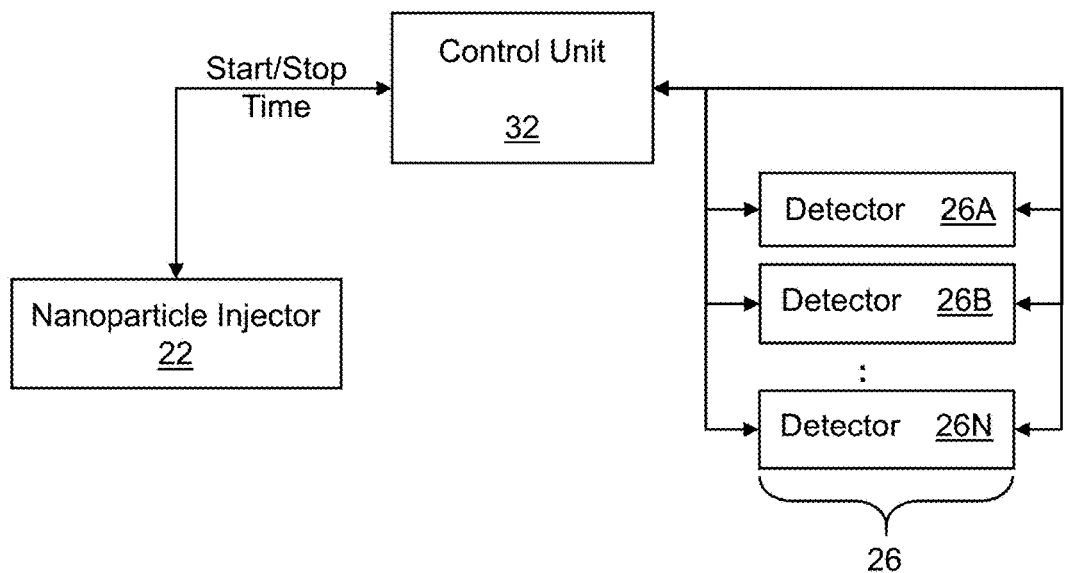
FIG. 8
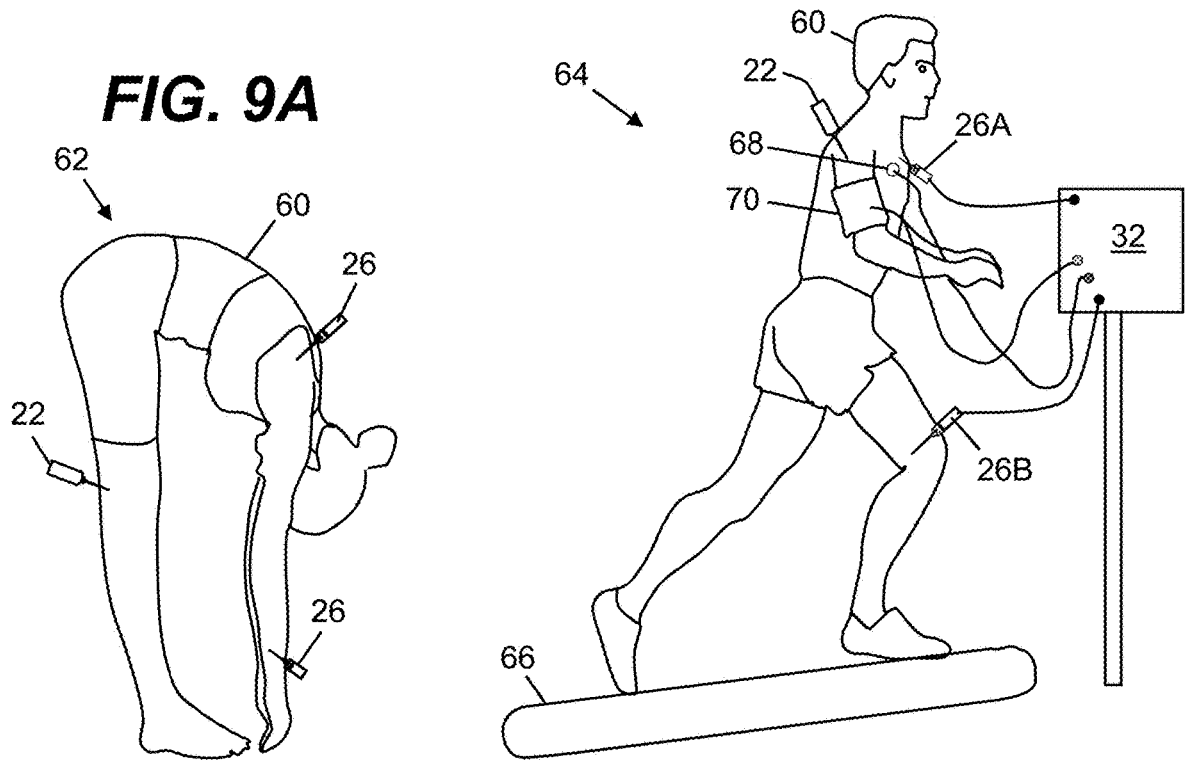
FIG. 9A
FIG. 9B

FLUORESCENT SENSING FOR EVALUATING FLUID

REFERENCE TO RELATED APPLICATIONS

The present patent application is a continuation application of U.S. patent application Ser. No. 15/829,323, filed on 1 Dec. 2017, which claims the benefit of U.S. Provisional Application No. 62/429,137, filed on 2 Dec. 2016, both of which are hereby incorporated by reference.

TECHNICAL FIELD

The disclosure relates generally to evaluating the flow of fluid through a conduit carrying the fluid, and more specifically, to a solution for using radiation, fluorescence, and nanoparticles, to evaluate the flow of the fluid in the conduit.

BACKGROUND ART

There are a multitude of approaches for evaluating the flow of fluid through a conduit. Blood vessels that carry the bloodstream of a living body such as a human or animal are one type of conduit where it is desirable to evaluate the flow of fluid, as characteristics of the blood flow in any given tissue are a good indicator of that tissue's health. Some conditions, like infection and inflammation, can lead to an increase in local blood flow, whereas others, like atherosclerosis, heart failure, and diabetes, can cause a decrease. Precisely and even continuously monitoring blood flow enables doctors to better tailor care to individual patients and conditions.

Various devices are available for sensing parameters in the bloodstream of a human such as the blood flow rate. The most common arrangement for measuring the blood flow rate is by introducing a catheter including a sensor element into body tissue of a patient. This approach is somewhat problematic, since the sensor element may be positioned outside an intended blood vessel which can result in erroneous measurements. Other approaches involve minimally invasive monitoring of the blood flow rate but these too suffer from inaccurate measurements.

SUMMARY OF THE INVENTION

This Summary Of The Invention introduces a selection of certain concepts in a brief form that are further described below in the Detailed Description Of The Invention. It is not intended to exclusively identify key features or essential features of the claimed subject matter set forth in the Claims, nor is it intended as an aid in determining the scope of the claimed subject matter.

Aspects of the present invention are directed to evaluating the flow of fluid through a conduit using radiation, fluorescence, and nanoparticles. The various embodiments of the present invention are suitable for a multitude of different types of fluids which can include liquids and gases. For example, the embodiments have utility with fluids that have some viscosity and are compressible in nature (e.g., petrol, kerosene), fluids that have some viscosity that is dependent on temperature and pressure (e.g., water, air), plastic fluids, and biological fluids. In addition, the various embodiments are suitable for a multitude of different types of conduits that can carry, distribute and transport fluids. For example, the conduits can include any vessels, channels, piping, and tubing that carry fluids. In one embodiment, blood vessels (e.g., arteries, veins and capillaries) in a living body such as a human and animal can serve as a network of conduits that carry distribute and transport a biological fluid such as blood throughout the body.

A fluid flow evaluation system according to embodiments of the present invention can include a nanoparticle injector configured to inject nanoparticles into the fluid flowing through the conduit. The nanoparticle injector can include, but is not limited to, a syringe. The type of nanoparticle injector that is used will depend on the type of fluid, the conduit that is used to carry the fluid, as well as the type of nanoparticles that are used for injection into the conduit.

The nanoparticles injected into the flow of the fluid in the conduit can include a variety of different types of nanoparticles. For example, the nanoparticles can vary by size, shape, and structure. In one embodiment, each of the nanoparticles can include a magnetic core and a fluorescent shell enclosing the magnetic core, such that the fluorescent shell is configured to have an emission of fluorescence in response to an applied external magnetic field. In an embodiment in which the fluid is a biological fluid and the conduit is a vessel or network of vessels within a human body or animal body that circulates the fluid, the nanoparticles can be configured to bind to different cells within the body. In another embodiment, the nanoparticles can include a dosage of medication that can be activated for delivery to specified sections of the body.

The fluid flow evaluation system according to embodiments of the present invention can further include a detector configured to determine the presence of the nanoparticles at various locations within the conduit. In one embodiment, the detector can include a radiation source configured to irradiate the fluid with a target radiation. The radiation source can include, but is not limited to, an ultraviolet radiation source, a visible light source, an infrared source, and/or a terahertz radiation source. The detector can further include a fluorescent meter configured to measure an amount of fluorescence emitted from the fluid in response to being irradiated with the radiation. The fluorescent meter can include, but is not limited to, a photodetector, a visible light camera, and/or a terahertz camera. In one embodiment, the fluorescent meter can sense a fluorescent signal emitted from the fluid in response to being irradiated with the radiation. Generally, the fluorescent signal is an indication of the presence of nanoparticles at a particular location that the detector is positioned about the conduit. The fluorescent meter can also record a time that the detector senses the presence of nanoparticles and a shape of an impulse response signal at the time of detection that is representative of the injection of the plurality of nanoparticles into the conduit at an injection site.

The nanoparticle injector and the detector can be positioned with respect to each other in one of a variety of arrangements. In one embodiment, the nanoparticle injector and the detector can be located in close proximity to each other. In one embodiment, the nanoparticle injector and the detector can be integrated with each other as a monolithic unit. In one embodiment, the radiation source and the fluorescent meter are spaced apart from each other by a predetermined distance, wherein the predetermined distance is less than the fluid flow within the conduit multiplied by a fluorescence lifetime of the emittance fluorescence.

The fluid flow evaluation system according to embodiments of the present invention can further include a control unit configured to determine the flow of the fluid in the conduit as well as other parameters associated with the nanoparticles (e.g., density) as a function of the measured amount of fluorescence. In one embodiment, the control unit can determine the flow rate of the fluid through the conduit as a function of a time that the nanoparticle injector injects and stops injecting the nanoparticles into the conduit, the shape of the impulse response signal at the injection site, the time that the detector detects the presence of the nanoparticles, and/or the shape of the impulse response signal at the time of detection. The control unit can determine the density of the nanoparticles in the fluid flow as a function of the shape of the impulse response signal at the injection site and at the location of the detector.

A fluid flow evaluation system according to one embodiment can include a detector that utilizes a fluid withdrawing device that is configured to withdraw a sample of fluid from the flow of the fluid. In this manner, the radiation source can irradiate the fluid withdrawn by the fluid withdrawing device with the target radiation. The fluid withdrawing device can include, but is not limited to, a syringe. The type of fluid withdrawing device that is used will depend on the type of fluid and the conduit that is used to carry the fluid, as well as the nanoparticles that are in the stream of fluid. In one embodiment, the radiation source and the fluorescent meter can be spaced apart from the fluid withdrawing device. In one embodiment, the radiation source and the fluorescent meter can be integrated with the fluid withdrawing device.

The fluid flow evaluation systems of the various embodiments have a wide variety of applications of use. For example, the various fluid flow evaluation systems described herein can be used in a medical scenario to evaluate the flow of a biological fluid. In one embodiment, in which the blood vessels within a human or animal body serve as a network of conduits that carry, distribute, and transport blood throughout the body, the nanoparticle injector can inject the nanoparticles at an injection site in the circulatory system that is proximate an artery that supplies blood from the heart to other parts of the body, while the detector can include a plurality of detectors that are located about different positions accessing the network of blood vessels. The nanoparticle injector and the detectors can take the form of medical instruments that are adapted for insertion with the blood vessels. In one embodiment, the detectors can operate in vivo with the blood vessels, wherein each radiation source irradiates radiation into the bloodstream and each fluorescent meter measures the fluorescence emitted from the blood. In one embodiment, the radiation source and the fluorescent meter of each detector can be integrated with a medical instrument adapted for insertion with the blood vessels, such that the radiation source and the fluorescent meter evaluate the blood after irradiation into the stream through a waveguide and removal from the vessel with a device like a fluid withdrawing device.

The control unit can determine the flow of blood within the network of blood vessels as a function of the measured amount of fluorescence ascertained by the detectors. In this manner, the control unit can evaluate the determined flow rate and the data from each of the detectors with experimental data to ascertain an ability of the vessels to transmit the blood through the network. In addition, the control unit can ascertain the blood flow measurements at different body positions. In one embodiment, the control unit can determine an effect that certain external influences have on the flow of blood in the circulatory system of a body, including but not limited to, the blood pressure, pulse rate, temperature, respiration, electrical activity from the heart, proximity to consumption of food, and/or administration of a medical modality.

A first aspect of the invention provides a system, comprising: a nanoparticle injector configured to inject a plurality of nanoparticles into fluid flowing through a conduit; a detector configured to determine a presence of the nanoparticles in the fluid, the detector including: a radiation source configured to irradiate at least a portion of the fluid with radiation; and a fluorescent meter configured to measure an amount of fluorescence emitted from the at least the portion of fluid irradiated with the radiation; and a control unit configured to determine a set of attributes corresponding to a flow of the fluid through the conduit as a function of the measured amount of fluorescence.

A second aspect of the invention provides a system, comprising: a nanoparticle injector configured to inject a plurality of nanoparticles into a biological fluid flowing through a network of conduits at an injection site; a plurality of detectors located about the network of conduits, each detector configured to detect a presence of nanoparticles in a location that the detector is positioned about the network of conduits, each detector including: a fluid withdrawing device configured to withdraw a sample of biological fluid from the flow of the biological fluid at the location that the detector is positioned; an ultraviolet radiation source configured to irradiate the sample of biological fluid withdrawn by the fluid withdrawing device with ultraviolet radiation; and a fluorescent meter configured to sense a fluorescent signal emitted from the sample of biological fluid irradiated with the ultraviolet radiation, the fluorescent signal indicative of the presence of nanoparticles at the location that the detector is positioned about the network of conduits; and a control unit operatively coupled to the nanoparticle injector and the plurality of detectors to determine a flow rate of the fluid through the network of conduits, the control unit determining the flow rate of the fluid through the network of conduits as a function of a time that the nanoparticle injector injects and stops injecting the plurality of nanoparticles into the network of conduits, a shape of an impulse response signal at the injection site, a time that each of the plurality of detectors detects the presence of the nanoparticles, and a shape of an impulse response signal at the time of detection by each of the plurality of detectors.

A third aspect of the invention provides a system for evaluating fluid flow of a biological fluid moving through a network of vessels within a biological system of a human body, comprising: a nanoparticle injector configured to inject a plurality of nanoparticles into the biological fluid flowing through the network of vessels at an injection site, each of the nanoparticles including a dosage of medication attached thereto; a plurality of detectors located about the network of vessels, each detector configured to detect a presence of nanoparticles in a location that the detector is positioned about the network of vessels, each detector including: a fluid withdrawing device configured to withdraw a sample of biological fluid from the flow of the biological fluid at the location that the detector is positioned; an ultraviolet radiation source configured to irradiate the sample of biological fluid withdrawn by the withdrawing device with ultraviolet radiation; a fluorescent meter configured to sense a fluorescent signal emitted from the sample of biological fluid irradiated with the ultraviolet radiation, the fluorescent signal indicative of the presence of nanoparticles at the location that the detector is positioned; and a medication activation device that is configured to activate a release of the medication from the nanoparticles at the location that the detector is positioned about the network of vessels; and a control unit operatively coupled to the nanoparticle injector and the plurality of detectors, the control unit configured to perform a fluorescent analysis of the sample of biological fluid in the network of conduits, the fluorescent analysis including determining a flow rate of the biological fluid through the network of vessels and a density of the nanoparticles in the fluid flow of the biological fluid at each location that the plurality of detectors are positioned about the network of vessels, the control unit further configured to direct the medication activation devices at specified locations about the network of vessels to activate the release of the medication from the plurality of nanoparticles for absorption in the network and transmission thereabout as a function of the fluorescence analysis.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIG. 1A shows an illustrative heart with a blocked artery, while

FIG. 8 shows a schematic block diagram of a control unit operating with a fluid flow evaluation system like the one depicted in FIG. 6 that includes a nanoparticle injector that releases nanoparticles in a network of conduits and a plurality of detectors positioned about the network to detect the presence of the nanoparticles, that performs a fluorescent analysis to obtain fluid and nanoparticle metrics according to an embodiment.

FIGS. 9A-9B show schematic views of fluid flow evaluation systems for evaluating a flow of biological fluid in a human body at different body positions and levels of activity according to embodiments.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1A:
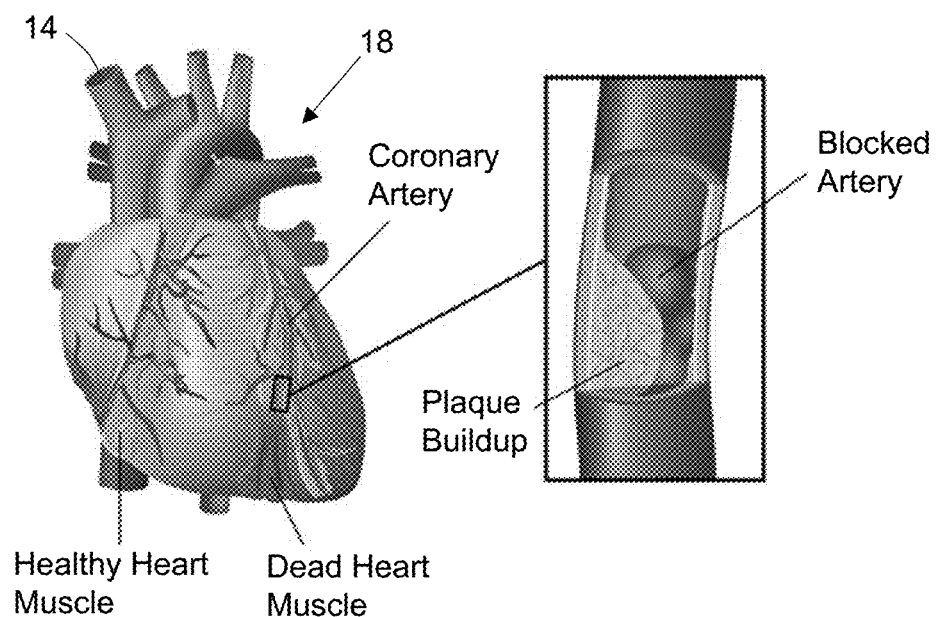

As indicated above, aspects of the invention are directed to evaluating the flow of fluid through a conduit using radiation, fluorescence, and nanoparticles. As used herein, a fluid is a substance that continually deforms or flows under an applied shear stress. A fluid can be a liquid, gas, plasma, and to some extent, a plastic solid. The various embodiments of the present invention are described in relation to biological fluids, which as used herein means any bio-organic fluid produced by an organism that can be excreted, secreted, obtained or developed as a result of a pathological process. A non-exhaustive list of biological fluids includes blood, cerebrospinal fluid, pleural fluid, sweat, tears, milk, etc. As used herein, biological fluids also include medical fluids that are developed for and used in individual life forms. A non-exhaustive list of medical fluids that are covered by the term biological fluid includes insulin, feed solutions, and injectable and intravenously supplied medication. Although the various embodiments are directed to biological fluids, it is understood that aspects of the invention are suitable for use with a multitude of different types of fluids, including fluids that have some viscosity and are compressible in nature (e.g., petrol, kerosene), fluids that have some viscosity but that are dependent on temperature and pressure (e.g., water, air), and plastic fluids, and the corresponding conduits through which such fluids can flow in a system.

The various embodiments of the present invention are described in relation to the flow of biological fluids within conduits flowing through or into a living body such as a human or an animal. Generally, the conduits flowing through the living body can include any of the multitude of networks within the body where biological fluids flow. For example, the circulatory system of a body contains blood vessels (e.g., arteries, veins, capillaries) in which blood is transported through the body. Other fluid systems within a living body such as a human and an animal can include, but are not limited to, the respiratory system which transports air, oxygen, and other gases to various parts of the body, the urinary system that eliminates waste from the body, and the lymphatic system that circulates lymph fluid through lymphatic vessels. All of these vessels and pathways within the body that carry, transport, and distribute biological fluids are analogous to conduits in which the aspects of the present invention are suitable for use therewith. Similarly, these aspects of the invention are applicable to conduits associated with medical instruments and devices (e.g., catheters, tubing, syringes, surgical tools, needles, etc.) that extract and/or deliver biological fluids from/to any one of the systems in the body. Although the various embodiments of the present invention are directed to evaluating the flow of fluid through conduits associated with internal vessels and channels within a living body or delivered to these vessels and channels, the aspects of the invention are applicable to other conduits which can include, but are not limited to, other channels, piping, and tubing all of which can carry, distribute and transport fluids.

As described below in more detail, the fluid flow evaluation systems of the various embodiments can evaluate the flow of the fluid using radiation. Ultraviolet radiation is one form of radiation that the fluid flow evaluation systems of the various embodiments can use to evaluate the flow of a fluid in a conduit. Ultraviolet radiation, which can be used interchangeably with ultraviolet light, means electromagnetic radiation having a wavelength ranging from approximately 10 nm to approximately 400 nm. Within this range, there is ultraviolet-A (UV-A) electromagnetic radiation having a wavelength ranging from approximately 315 nm to approximately 400 nm, ultraviolet-B (UV-B) electromagnetic radiation having a wavelength ranging from approximately 280 nm to approximately 315 nm, and ultraviolet-C (UV-C) electromagnetic radiation having a wavelength ranging from approximately 100 nm to approximately 280 nm.

As used herein, a material/structure is considered to be "reflective" to ultraviolet light of a particular wavelength when the material/structure has an ultraviolet reflection coefficient of at least 30 percent for the ultraviolet light of the particular wavelength. A highly ultraviolet reflective material/structure has an ultraviolet reflection coefficient of at least 80 percent. Furthermore, a material/structure/layer is considered to be "transparent" to ultraviolet radiation of a particular wavelength when the material/structure/layer allows at least ten percent of radiation having a target wavelength, which is radiated at a normal incidence to an interface of the material/structure/layer to pass there through. Also, unless otherwise noted, the term "set" means one or more (i.e., at least one) and the phrase "any solution" means any now known or later developed solution.

The fluid flow evaluation systems of the various embodiments described herein can include a number of components described herein in more detail that facilitate the analysis and evaluation of the fluid within a conduit. The modalities used with the various fluid flow evaluation systems described herein including its respective components can include any now known or later developed approaches that incorporate the concepts of the embodiments described below in more detail.

Figure 1B:
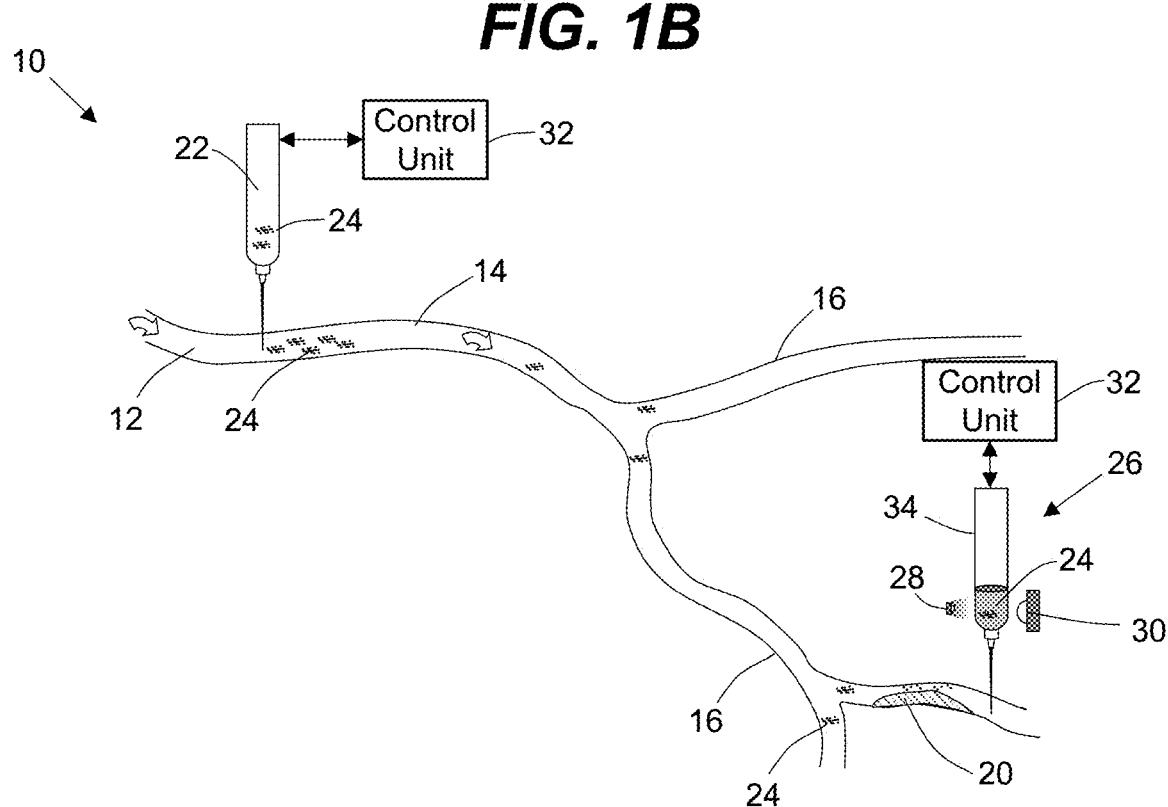
FIG. 1B shows a schematic view of a fluid flow evaluation system for evaluating a flow of fluid through a conduit having multiple branches according to an embodiment.

Turning to the drawings, FIG. 1B shows a schematic view of a fluid flow evaluation system 10 for evaluating a flow of fluid 12 through a conduit 14 having multiple branches 16 according to an embodiment. In this embodiment, as illustrated by FIG. 1A, the fluid 12 can include a biological fluid such as, for example, blood pumped through a conduit 14 that can include a network, branches, or series of blood vessels coupled to a heart 18. As an example, the heart 18 depicted in FIG. 1A is characterized as having a healthy heart muscle and a dead heart muscle with cholesterol plaque buildup that has caused a blood clot that blocks a coronary artery. An example of the plaque buildup is shown in a portion of the vessel 14 and is designated with the reference element 20. It is understood that FIGS. 1A-1B are only illustrative of one possible scenario that is representative of a portion of a blood vessel, and is not meant to limit any of the various embodiments of the present invention, but instead is meant to explain a setting which the embodiments are suitable for use therein.

As shown in FIG. 1B, the fluid flow evaluation system 10 can include a nanoparticle injector 22 that is configured to inject a plurality of nanoparticles 24 into the fluid (e.g., blood) 12 flowing through the conduit (e.g., vessel) 14. The nanoparticle injector 22 can include, but is not limited to, a syringe. It is understood that the type of nanoparticle injector 22 that is used will depend on the type of fluid 12, the conduit 14, and the nanoparticles 24.

As used herein, nanoparticles means particles having a largest dimension of one micron or less. The nanoparticles 24 as described herein in more detail, e.g., with regard to FIGS. 10A-10B can vary by size, shape, and structure. The nanoparticles 24 can be formed of any material that is safe for injection into the blood vessels of an animal, and more particularly, a human, at the desired dosing level. In the embodiment illustrated in FIG. 1B, the nanoparticles 24 can be configured to bind with antibodies that are typically present in the proximity of plaque buildup 20 within the blood vessels 14. In another embodiment, the nanoparticles 24 can be configured to have medication that can be activated for release in the proximity of the plaque buildup 20 within the proximity of the vessels. Details of these embodiments are described herein in more detail, e.g., with respect to FIGS. 11A-11B, 12 and 13. In other embodiments which relate to use with one of the systems within a living body that supply, transport, and distribute biological fluids, the nanoparticles can be configured to bind to the antibodies that are typically present in the proximity of cancer cells.

FIG. 1B shows that the fluid flow evaluation system 10 can further include a detector 26 that is configured to determine the presence of the nanoparticles 24 at various locations within the conduit (e.g., vessel) 14. In one embodiment, the detector 26 can include a radiation source 28 that is configured to irradiate the fluid 12 with a target radiation. The radiation source 28 can include, but is not limited to, an ultraviolet radiation source that emits ultraviolet radiation, a visible light source that generates visible light, an infrared radiation source that emits infrared radiation, and/or a terahertz radiation source that generates terahertz radiation. Although FIG. 1B shows the detector 26 with one radiation source 28, it is understood that more than one radiation source can be used such as for example, an array of radiation sources. Also, it is understood that one or more of the above-identified radiation sources can operate in conjunction to irradiate the fluid 12 with radiation. These radiation sources can be located at the same position or at varying locations.

In one embodiment, the radiation source 28 utilized with the detector 26 can include at least one ultraviolet radiation source that emits ultraviolet radiation towards the biological fluid 12. The ultraviolet radiation source can include any combination of one or more ultraviolet radiation emitters. Examples of ultraviolet radiation emitters can include, but are not limited to, high intensity ultraviolet lamps (e.g., high intensity mercury lamps), discharge lamps, ultraviolet light emitting diodes (UV LEDs), super luminescent LEDs, laser diodes, and/or the like. In one embodiment, the ultraviolet radiation source can include an ultraviolet light emitting diode that includes a solid state semiconductor device based on a group III nitride semiconductor material. In one embodiment, the ultraviolet radiation source can include a set of LEDs manufactured with one or more layers of materials selected from the group III nitride material system (e.g., $Al_xIn_yGa_{1-x-y}N$, where $0 \leq x, y \leq 1$, and $x+y \leq 1$ and/or alloys thereof). Additionally, the ultraviolet radiation source can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like. Illustrative wave guiding structures include, but are not limited to, a wave guide, a plurality of ultraviolet fibers, each of which terminates at an opening, a diffuser, and/or the like.

The ultraviolet radiation source(s) can be configured to operate at a number of wavelengths. For example, in one embodiment, the ultraviolet radiation source(s) can be configured to operate at a wavelength that ranges from about 260 nm to about 310 nm, with 250 nm to 290 nm being a preferred range. In one embodiment, in which the detector 26 utilizes more than one ultraviolet radiation source, these sources can be configured to function in a coordinated manner. For example, the ultraviolet radiation sources can operate at the same wavelengths and intensities for the same duration, or the sources can operate at different wavelengths and intensity for varying durations. In one embodiment, several different types of nanoparticles can be injected into a fluid channel within a person's body (such as a blood vessel). Each type of nanoparticle can have a corresponding fluorescence and can be excited by a particular ultraviolet (UV) or near-UV radiation excitation. In an embodiment, for efficient excitation of all the nanoparticles present, several sources operating at different wavelengths and intensities can be used. In an embodiment, the nanoparticles can be fabricated to have particular surface properties, with each type of nanoparticle traveling at a particular rate through the fluid channel. In this case, a first set of ultraviolet radiation sources can operate at a target wavelength and intensity that is designed to irradiate a first type of nanoparticle, while a second set of ultraviolet radiation sources can operate at a different target wavelength and intensity that is designed to irradiate a second type of nanoparticle.

The detector 26 can further include a fluorescent meter 30 that is configured to measure an amount of fluorescence emitted from the fluid 12 irradiated with the radiation. The fluorescent meter 30 can include, but is not limited to, a photodetector, a visible light camera, and/or a terahertz camera. In one embodiment, the fluorescent meter 30 can sense a fluorescent signal emitted from the fluid 12 in response to being irradiated with the radiation. The fluorescent signal is an indication of the presence of nanoparticles 24 at a particular location that the detector 26 is positioned about the network of vessels 14. The fluorescent meter 30 and/or the control unit 32 can also record a time that the fluorescent meter 30 senses the presence of nanoparticles and a shape of an impulse response signal at the time of detection. As used herein, an impulse response signal is a signal having a beginning and an ending, which can be characterized, for example, by a packet of nanoparticles released into a fluid stream. In the various embodiments described herein, the impulse response signal is representative of the injection of the plurality of nanoparticles 24 into the fluid 12 flowing through the conduit 14 at an injection site.

The positioning of the radiation source 28 and the fluorescence meter 30 can include one of a number of different configurations. For example, the radiation source 28 and the fluorescent meter 30 can be spaced apart from each other by a predetermined distance. In one embodiment, the predetermined distance is less than the fluid flow within the conduit (e.g., vessel) 14 multiplied by a fluorescence lifetime of the emittance fluorescence emitted from a nanoparticle irradiated by radiation from the radiation source 28. In one embodiment, the radiation source 28 and the fluorescent meter 30 can be integrated with each other as a monolithic unit. In one embodiment, the radiation source 28 and the fluorescent meter 30 can take the form of two separate units that constitute the detector 26. These two separate units can be separated by a predetermined distance along the conduit 14. For example, in the embodiment depicted in FIG. 1B, the radiation source 28 and the fluorescent meter 30 can have a separation distance that ranges from 100 nanometers to 100 microns. Those skilled in the art will appreciate that the selected difference separating the radiation source 28 and the fluorescent meter 30 is variable and will depend on the particular application of use of the flow evaluation system.

The positioning of the nanoparticle injector 22 and the detector 26 can also include one of a number of different configurations. For example, the nanoparticle injector 22 and the detector 26 can be located in close proximity to each other. As used in this context, "in close proximity" means within a range between a few millimeters to a few centimeters (i.e., five centimeters or less). In another embodiment, the nanoparticle injector 22 and the detector 26 can be integrated with each other as a monolithic unit. In this manner, the nanoparticle injector 22 and the detector 26 can be adjacent to each in a monolithic unit.

As shown in FIG. 1B, the fluid flow evaluation system 10 can include a control unit 32 that is configured to determine a presence of the nanoparticles in the conduit 14 as a function of the measured amount of fluorescence by the detector 26. In one embodiment, the control unit 32 can determine the flow rate of the fluid 12 through the conduits 14. For example, the control unit 32 can determine the flow rate of the fluid 12 through the conduit 14 as a function of a time that the nanoparticle injector 22 injects and stops injecting the plurality of nanoparticles 24 into the conduit 14, the shape of the impulse response signal at the injection site, the time that the detector 26 detects the presence of the nanoparticles, and the shape of the impulse response signal at the time of detection by the detector.

In one embodiment, the control unit 32 can include a timer to operate in conjunction with the nanoparticle injector 22 and the detector 26. The timer can record the time that the nanoparticle injector 22 injects the nanoparticles into the fluid 12 flowing through the conduit 14. The timer can also record the time that the nanoparticle injector 22 stops injecting the nanoparticles into the fluid 12 and the time that the detector 26 detects the presence of the nanoparticles in the fluid 12 based on the emittance measurements obtained by the fluorescent meter 30. In addition, the timer can record the shape of the impulse response signal at the injection site and the shape of the impulse response signal at the time of detection by the detector.

The control unit 32 is also configured to detect a density of the nanoparticles in the fluid flow at the location that the detector is positioned about the network of conduits 14. In general, the control unit 32 can determine the density of the nanoparticles in the fluid flow as a function of the shape of the impulse response signal at the injection site and the location of the detector. More specifically, the control unit 32 can infer the density of nanoparticles from the fluorescence intensity of the fluid at the location of the detector at the time of measurement.

In one embodiment, the nanoparticle injector 22, the detector 26 including the radiation source 28 and the fluorescent meter 30, and the control unit 32 can operate in conjunction to analyze and evaluate the biological fluid 12 (e.g., blood) that is flowing through the network of conduits 14 (e.g., blood vessels) in the following manner. First, the timer of the control unit 32 will record the time that the nanoparticle injector 22 starts releasing the nanoparticles in the fluid 12 flowing through the network of conduits 14. Next, the timer will record the time that the nanoparticle injector 22 stops releasing the nanoparticles into the fluid 12. The timer will then record the time that the detector 26 detects the arrival or presence of nanoparticles at the detector. Based on this information the control unit 32 can then determine the flow of the fluid 12. In particular, the control unit 32 determines the flow of the fluid 12 by measuring the time between the release and detection of nanoparticles and a known distance between the release location and the detector location. In general, the detection is based on the fluorescence intensity.

In addition to determining the flow of the fluid 12, the control unit 32 can determine the density of the nanoparticles in the aforementioned manner. After determining the density of the particles, the control unit 32 can compare the density to a predetermined threshold value which is indicative of how the nanoparticles are spreading throughout the fluid channel as they travel from the injector to the detector. For instance, if nanoparticles do not significantly spread as they travel, the detector will receive a high intensity fluorescent signal followed by an abrupt termination of such signal. In cases when nanoparticles significantly spread, the fluorescent signal will be wide and slowly decaying through time during measurement. In one embodiment, the timer can record the time that the nanoparticle density decreases below the predetermined threshold value. The control unit 32 can use this time that the nanoparticle density is less than the predetermined threshold to determine that most nanoparticles have been detected. For instance, the threshold value can be 1-5% of a maximum fluorescent value at the peak of fluorescent detection.

After making the above determinations, the control unit 32 can evaluate the flow rate and the data based thereon from the detector with experimental data to ascertain an ability of the network of conduits 14 to transmit the biological fluid 12 there through. In one embodiment, the experimental data can be obtained by comparing the measurements with similar measurements from one or more representative networks of conduits, e.g., from healthy subjects. In one embodiment, the control unit 32 can ascertain the ability of the network of conduits 14 to transmit the biological fluid from the measured data and the experimental data by comparing the flow rates between the present and representative networks of conduits. In addition, the flow rates can be further correlated with other medical observations, such as observations from the catheter, ultrasound, CAT scan, or MRI.

It is understood that the control unit 32 can perform a multitude of other functions. For example, the control unit 32 can control the irradiation of the fluid 12 with the radiation by the radiation source 28. In one embodiment, the control unit 32 can direct the radiation source 28 by controlling a plurality of operating parameters for irradiating the fluid. The operating parameters can include a wavelength of the radiation that is emitted from the radiation source 28, an intensity or dosage of the radiation delivered to the biological fluid by the radiation source and a treatment time that the source delivers the radiation to the biological fluid. Other parameters can include a power setting for operating the radiation source 28, and a maximum operating temperature of the radiation source.

In one embodiment, the control unit 32 can manage the duration that the radiation source is on for a particular application and ensure that radiation is applied to the biological fluid for that duration. The duration and frequency treatment that the radiation source is utilized can depend on detected condition signals provided to the control unit by the fluorescent meter 30 and the nanoparticle injector 22. In general, activating the operation of the radiation source 26 by the control unit 32 can include specifying any combination of one or more of the operating parameters (e.g., wavelength, intensity or dosage, and a treatment time). Other operating parameters can include an angular distribution of the radiation transmitted from the radiation source, a power setting for operating the radiation source, and a maximum operating temperature for the irradiation. It is understood that these operating parameters are illustrative of some of the parameters that can be set by the control unit 32 and is not meant to be limiting as other parameters exist which may be specified.

During operation of the radiation source 28, the control unit 32 can be used to control at least one of a plurality of predetermined radiation characteristics associated with the radiation emitted from the radiation source. The predetermined radiation characteristics that can be controlled by the control unit 32 can include wavelength, intensity, duration, and/or the like.

The control unit 32 can also include a wireless transmitter and receiver that is configured to communicate with a remote location via WiFi, BLUETOOTH, and/or the like. As used herein, a remote location is a location that is physically apart from the fluid flow evaluation system. For example, a remote computer can be used to transmit operational instructions to the wireless transmitter and receiver. The operational instructions can be used to program functions performed and managed by the control unit 32. In another embodiment, the wireless transmitter and receiver can transmit evaluation results to the remote computer.

The control unit 32 can include an input component and an output component to allow a user to interact with the fluid flow evaluation system 10 and the control unit, and to receive information therefrom. In one embodiment, the input component can permit a user to adjust at least one of the aforementioned plurality of operating parameters. In one embodiment, the input component can include a set of buttons and/or a touch screen to enable a user to specify various input selections regarding the operating parameters. In one embodiment, the output component can include a visual display for providing status information on the evaluation of the fluid, a simple visual indicator that displays whether an evaluation is underway (e.g., an illuminated light) or if the evaluation is over (e.g., absence of an illuminated light).

It is understood that the fluid flow evaluation system 10 can include other sensors in addition to the fluorescent meter 30 that are used with the detector 26. Those skilled in the art will appreciate that the type and amount of sensors will depend on the type fluid that is being evaluated, the type of conduit that is carrying the fluid, as well as the application that the fluid flow evaluation system is being used in. Examples of other sensors that can be used include, but are not limited to, a temperature sensor, a chemical sensor, a radiation sensor (e.g., an ultraviolet dose counter or meter), a transparency sensor, a bacterial fluorescence sensor, etc. Each of these sensors could detect the level or amount of a particular parameter that each is intended to measure and send signals thereof to the control unit 32 which can control and monitor the operations performed by the fluid evaluation system 10. For example, a temperature sensor can detect the temperature of the fluid 12, a chemical sensor can detect a level of a particular chemical that is present in the fluid, a radiation sensor can detect a level of radiation that is present in the fluid, and a transparency sensor can evaluate the transparency of the fluid within the conduit. These sensors can be deployed along with any of the aforementioned types of radiation sources in any desired configuration.

The fluid evaluation system 10 can further include a power source that is configured to power each of the nanoparticle injector 22, the detector 26 including the radiation source 28 and the fluorescent meter 30, and the control unit 32. In one embodiment, the power source can take the form of one or more batteries, a vibration power generator that can generate power based on magnetic inducted oscillations or stresses developed on a piezoelectric crystal. In another embodiment, the power source can include a super capacitor that is rechargeable. Other power components that are suitable for use as the power source for the fluid evaluation system 10 and the control unit can include a mechanical energy to electrical energy converter such as a piezoelectric crystal, and a rechargeable device.

It is understood that the control unit 32 can be implemented within the fluid evaluation system 10 in one of a multitude of implementations. For example, as shown in FIG. 1B, the control unit 32 can be configured as a separate component that operates in conjunction with the nanoparticle injector 22 and the detector 26 including the radiation source 28 and the fluorescent meter 30. In one embodiment, the control unit 32 can be implemented in a functionally distributed manner with the nanoparticle injector 22 and the detector 26. For example, a portion of the control unit 32 can be implemented with both the nanoparticle injector 22 and the detector 26 to perform functions specific to those components. In one embodiment, this distributed arrangement of the control unit 32 can be extended to having a portion that is remote from the fluid evaluation system 10 to receive and transmit information to the decentralized portions of the control unit that reside with the nanoparticle injector 22 and the detector 26.

The fluid evaluation system 10 heretofore is described with the detector 26 including only the radiation source 28 and the fluorescent meter 30, however, it is understood that the detector can include other components as can the fluid evaluation system 10. For example, the detector 26 can include a fluid withdrawing device 34 that is configured to withdraw a sample portion of the fluid 12 from the flow of the fluid in the conduit 14. In this manner, the fluid withdrawing device 34, which can include, but is not limited to, a syringe, can operate in conjunction with the radiation source 28 and the fluorescent meter 30. For example, the radiation source 28 can be configured to irradiate the fluid 12 withdrawn by the fluid withdrawing device 34 with radiation, while the fluorescent meter 30 can collect the fluorescent emissions from the nanoparticles upon being irradiated. The data collected and obtained by the fluid withdrawing device 34, the radiation source 28, and the fluorescent meter 30 can be used by the control unit 32 to ascertain the flow rate of the fluid and the density of the nanoparticles. In one embodiment, the radiation source 28 and the fluorescent meter 30 can be spaced apart from the fluid withdrawing device 34. In another embodiment, the radiation source 28 and the fluorescent meter 30 can be integrated with the fluid withdrawing device 34 as schematically depicted in FIG. 1B.

Figure 2:
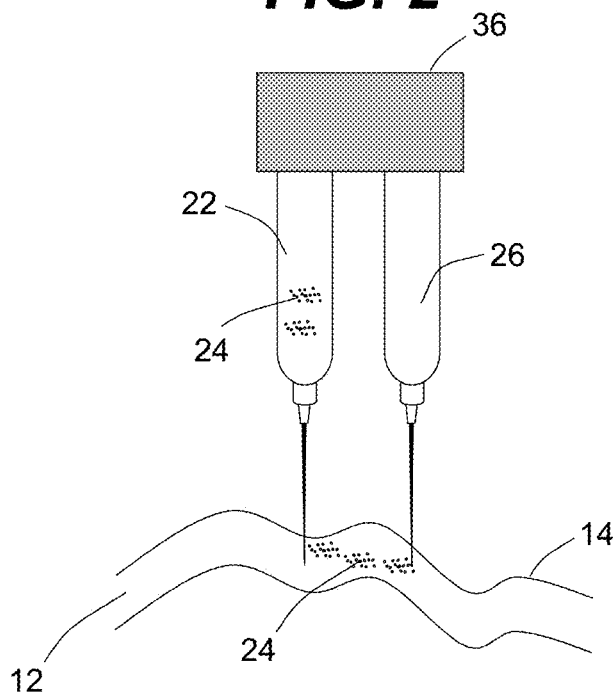
FIG. 2 shows a more detailed view of a nanoparticle injector and a detector depicted in FIG. 1B according to an embodiment.

FIG. 2 shows a more detailed view of the nanoparticle injector 22 and the detector 26 depicted in FIG. 1B according to an embodiment. In the embodiment depicted in FIG. 2, the nanoparticle injector 22 and the detector 26 are integrated in a monolithic unit 36 in close proximity (e.g., 1 cm apart or less) to each other within the unit. By having the nanoparticle injector 22 and the detector 26 in close proximity, the detector 26 can measure the differential flow speed of the fluid 12 in the conduit 14. In this embodiment, the nanoparticle injector 22 can inject the nanoparticles 24 into the fluid 12 flowing through the conduit 14, while the detector 26 irradiates the fluid with radiation emitted from a radiation source 28 (not shown in FIG. 2) and the fluorescent meter 30 (not shown in FIG. 2) measures the fluorescence emitted from the irradiated particles. The control unit 32 (not shown in FIG. 2) can determine the flow rate of the fluid and the density of the nanoparticles at the location of the detector 26 based on the fluorescence measurements. The control unit 32 can determine the differential flow speed by calculating how quickly the nanoparticles arrive at the detector.

Figure 3:
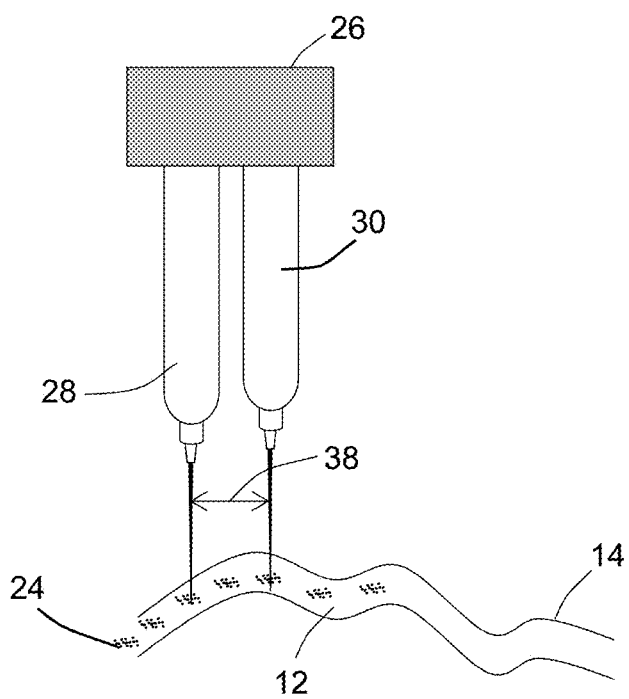
FIG. 3 shows a schematic view of a detector having a radiation source and a fluorescent meter according to an embodiment.

FIG. 3 illustrates another embodiment in which the differential flow speed of the fluid 12 can be measured at a location of the conduit 14. In the embodiment of FIG. 3, the detector 26 is shown with a radiation source 28 and a fluorescent meter 30. That is, the radiation source 28 and the fluorescent meter 30 form two separate units within the monolithic detector 26. Fluid may, or may not, be withdrawn at the location of the fluorescent meter 30. As shown in FIG. 3, the radiation source 28 and the fluorescent meter 30 can be separated from each other in the detector 26 by a distance 38 that maintains the components within close proximity (e.g., 1 cm apart or less). Like other embodiments described herein, the radiation source 28 can illuminate the nanoparticles 24 with the target light radiation and the fluorescent meter 30 can detect fluorescence from the nanoparticles because the nanoparticles 24 can have prolonged fluorescence after being irradiated at a target radiation at a first location. In one embodiment, the radiation source 28 and the fluorescent meter 30 can be spaced apart from each other by a predetermined distance 38 that is less than the fluid flow within the conduit 12 multiplied by the fluorescence lifetime of the emitted fluorescence. This spacing relationship between the radiation source 28 and the fluorescent meter 30 can be a few millimeters up to a few centimeters (i.e., five centimeters or less).

Figure 4:
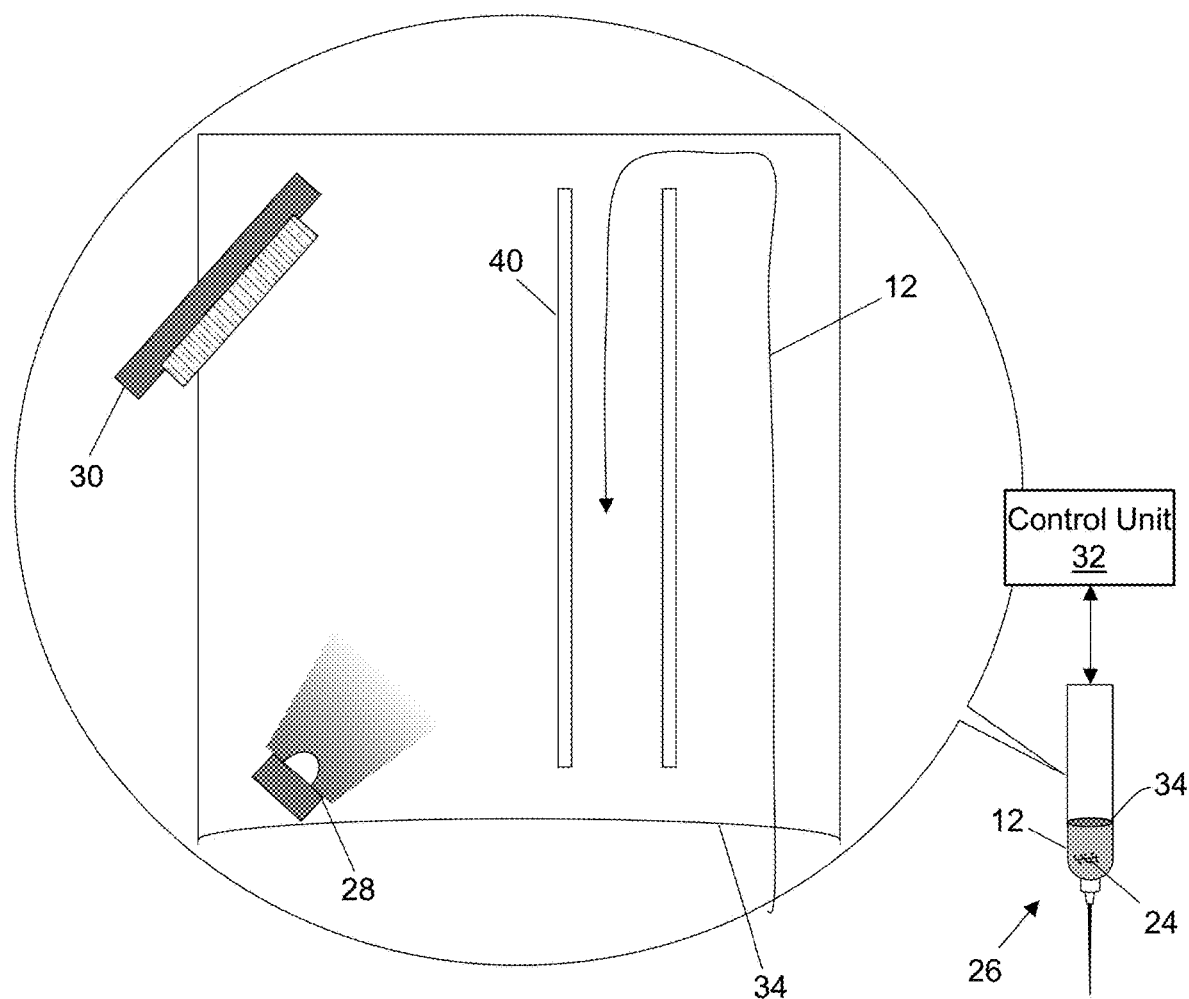
FIG. 4 shows a more detailed view of a detector with a radiation source, a fluorescent meter, and a fluid withdrawing device as an integrated unit according to an embodiment.

FIG. 4 shows a more detailed view of the detector 26 with a radiation source 28, a fluorescent meter 30 and a fluid withdrawing device 34 as an integrated unit according to an embodiment. In this embodiment, the radiation source 28, the fluorescent meter 30 and the fluid withdrawing device 34 operate in the manner described herein. For example, the radiation source 28 can irradiate the fluid 12 with radiation after the fluid withdrawing device 34 has withdrawn fluid 12 from a conduit, and the fluorescent meter 30 measures the fluorescence emitted from the irradiated particles. The exploded view of these components as depicted in FIG. 4 shows that the fluid withdrawing device 34 can include a channel 40 to direct the fluid 12 to the radiation source 28 and the fluorescent meter 30. It is understood that the fluid withdrawing device 34 can include other types of passageways that can direct the fluid 12 to the radiation source 28 and the fluorescent meter 30 besides the channel 40.

The detector 26 illustrated in FIG. 4 is well suited for use in many scenarios. For example, the detector 26 can be used in a fluid flow evaluation system in which blood flows in the blood vessels of a living body. In one embodiment, the fluid withdrawing device 34 can withdraw blood from a location that is "downstream" of an injection site in which nanoparticles are injected into the blood vessels. The radiation source 28 can irradiate the withdrawn blood with radiation such as ultraviolet radiation, and the fluorescent meter 30 can measure the fluorescence emitted from the irradiated particles. The control unit can receive the data from the detector 26 and can make several assessments therefrom such as, but not limited to, the flow rate of the blood, the density of the nanoparticles, and/or the like.

Figure 5:
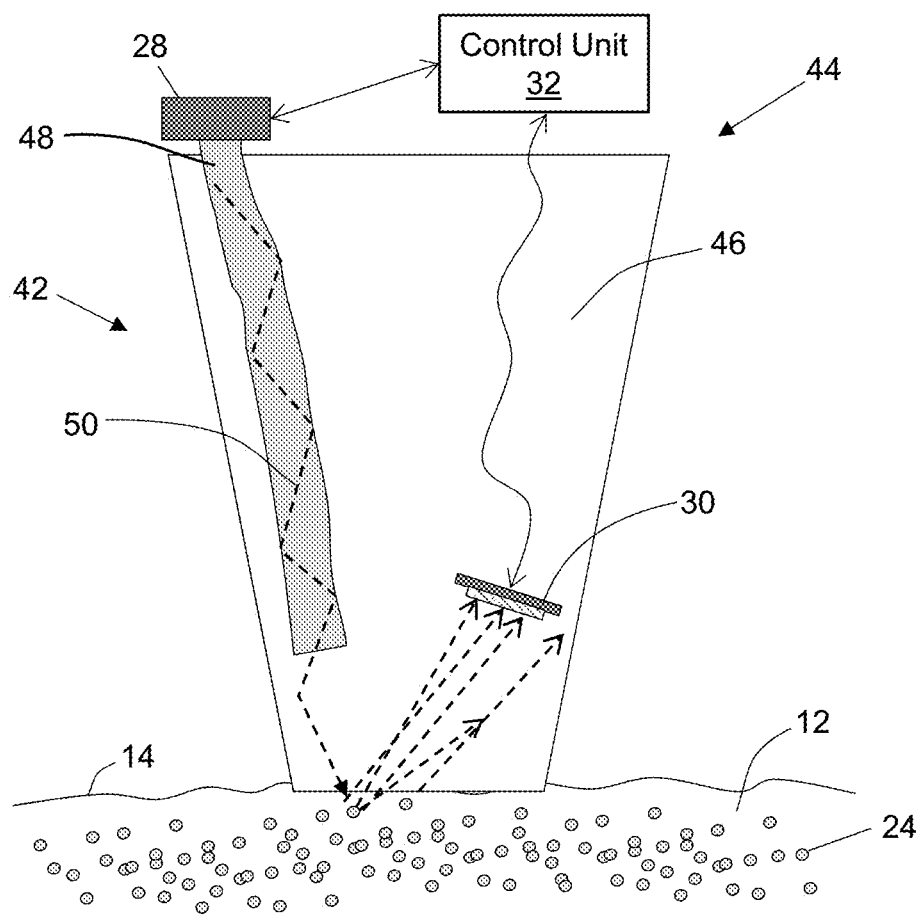
FIG. 5 shows a detailed view of a detector with a radiation source and a fluorescent meter operating in vivo with fluid flowing through a conduit according to an embodiment.

In scenarios in which the detector is used in a fluid evaluation system to evaluate blood, it may not be preferable to constantly draw and analyze blood for fluid analysis by the radiation source 28 and the fluorescent meter 30 which are located away from the network of blood vessels. In one embodiment, the fluid withdrawing device 34, the radiation source 28, and the fluorescent meter 30 can operate in vivo with the blood vessels. For example, FIG. 5 shows a detailed view of a detector 42 with a radiation source 28 and a fluorescent meter 30 operating in vivo with fluid such as blood flowing through a conduit like a blood vessel according to an embodiment. In one embodiment, the detector 42 can be incorporated in a medical instrument 44 that is adapted for insertion with the vessel 14. That is, both the radiation source 28 and the fluorescent meter 30 of the detector 42 can be integrated within the medical instrument 44. In one embodiment, the medical instrument 44 can include a blood collection device having a needle tip 46 that inserts into a blood vessel and a blood holding compartment that holds the blood.

As shown in FIG. 5, the detector 42 including the radiation source 28 and the fluorescent meter 30, can be incorporated into the needle tip 46 of the medical instrument 44. In one embodiment, a waveguide 48 can waveguide the radiation 50 emitted from the radiation source 28, which can be an ultraviolet radiation source, to the biological fluid (e.g., the blood) flowing through the vessel 14. The material forming the waveguide 48 can include, but is not limited to, a $SiO_2$, $Al_2O_3$, $CaF_2$, $MgF_2$, and/or other ultraviolet transparent media. As used herein, "to waveguide the radiation," "to light guide," or "wave guiding the radiation" means a mechanism by which radiation is guided from one location (e.g., an inlet of the waveguide) to another location (e.g., an outlet of the waveguide) without significant attenuation of the radiation.

In the embodiment depicted in FIG. 5, the waveguide 48 can waveguide the radiation 50 such as ultraviolet radiation from the radiation source 28, which can be an ultraviolet radiation source, to the blood 12 in the vessel, and the fluorescent meter 30 can be positioned within the needle tip 46 to measure the reflected signals from the nanoparticles 24 in the blood 12 of the vessel 14. In an alternative embodiment, an ultraviolet radiation source can be replaced with, or used in conjunction with at least one of a visible light source, an infrared radiation source, or a terahertz radiation source. As a result, the fluorescent meter 30 can be replaced with, or used in conjunction another type of fluorescent collector that is better suited for a visible light source, an infrared radiation source, and/or a terahertz radiation source, such as a visible light camera, an infrared camera, or a terahertz camera, respectively.

Figure 6:
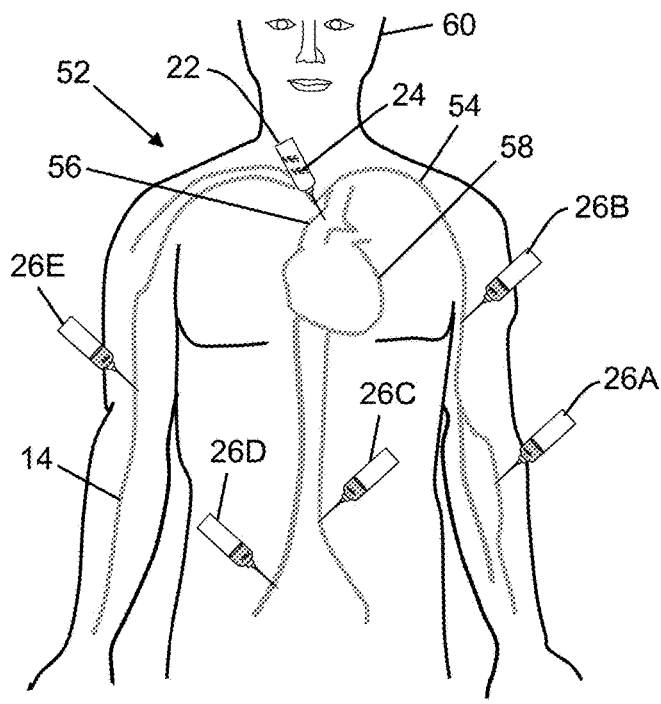
FIG. 6 shows a schematic view of a fluid flow evaluation system for evaluating a flow of biological fluid through a network of blood vessels with a nanoparticle injector that injects nanoparticles at an injection site and a plurality of detectors located about the network of vessels according to an embodiment.

FIG. 6 shows a schematic view of a fluid flow evaluation system 52 for evaluating a flow of biological fluid through a network 54 of blood vessels 14 with a nanoparticle injector 22 that injects nanoparticles 24 at an injection site 56 and a plurality of detectors 26 (e.g., 26A, 26B, 26C, 26D, 26E) located about the network of vessels according to an embodiment. In this embodiment, the nanoparticle injector 22 can inject the nanoparticles 24 into the blood flowing through the network of blood vessels 14 at the injection site 56 such as an artery near the heart 58 of a human 60. As shown in FIG. 6, the detectors 26 (e.g., 26A, 26B, 26C, 26D, 26E) can be located about the network 54 of blood vessels 14 at various locations that provide access to the vessels in the circulatory system of the human 60. In this manner, each detector 26 (e.g., 26A, 26B, 26C, 26D, 26E) can detect a presence of nanoparticles 24 in a location that the detector is positioned about the network 54 of blood vessels 14. It is understood that the number of detectors 26 depicted in FIG. 6 is only illustrative of one arrangement and is not meant to limit this embodiment or others described herein. For example, the fluid flow evaluation system 52 could deploy more or less detectors 26 than the number depicted in FIG. 6. Furthermore, a lower portion (e.g., legs and feet) of the human 60 which is not depicted in FIG. 6 could have detectors 26 to detect the presence of nanoparticles 24 in the portion of the network 54 of blood vessels 14. Also, it is understood that the nanoparticle injector 22 can be situated in another location relative to the heart 58.

In one embodiment, each of the detectors 26 (e.g., 26A, 26B, 26C, 26D, 26E) can have a fluid withdrawing device, a radiation source, and a fluorescent meter. For clarity, these components of the detectors 26 are not depicted in FIG. 6. As noted herein with regard to other embodiments, the fluid withdrawing device can withdraw a sample portion of blood from the flow of the bloodstream at the location that each detector is positioned. The radiation source associated with each detector, which can include an ultraviolet radiation source, can irradiate the blood withdrawn by the fluid withdrawing device with a target ultraviolet radiation. The fluorescent meter of each detector can sense a fluorescent signal emitted from the blood irradiated with the ultraviolet radiation. The fluorescent signal is indicative of the presence of nanoparticles 24 at the location that the detector is positioned about the network 54 of blood vessels 14. The fluorescent meter and/or the control unit 32 (not shown in FIG. 6) can be further configured to note a time that a detector 26 (e.g., 26A, 26B, 26C, 26D, 26E) senses the presence of nanoparticles 24 and a shape of an impulse response signal at the time of detection that is representative of the injection of the plurality of nanoparticles into the network of conduits at the injection site 56.

Although not depicted in FIG. 6, the fluid flow evaluation system 52 can further include a control unit 32 that is operatively coupled to the nanoparticle injector 22 and the plurality of detectors 26 (e.g., 26A, 26B, 26C, 26D, 26E) to determine a flow rate of the blood through the network 54 of blood vessels 14. The control unit can determine the flow rate of the fluid through the network 54 of blood vessels 14 as a function of a time that the nanoparticle injector 22 injects and stops injecting the nanoparticles 24 into the network, the shape of the impulse response signal at the injection site 56, the time that each of the detectors 26 (e.g., 26A, 26B, 26C, 26D, 26E) detects the presence of the nanoparticles, and the shape of the impulse response signal at the time of detection by each of the detectors.

While the illustrative embodiment shown in FIG. 6 includes a single nanoparticle injector 22 and multiple detectors 26, it is understood that embodiments can include multiple nanoparticle injectors 22. For example, in an alternative embodiment, multiple nanoparticle injectors 22 can be located throughout various locations of network 54 of blood vessels 14, with each nanoparticle injector 22 injecting nanoparticles into the blood vessels 14 that can be distinguished from the nanoparticles injected from other nanoparticle injectors 22. One or more detectors 26 can detect the nanoparticles as they arrive at a corresponding location in the network 54 of blood vessels 14 and determine from which location the nanoparticles were injected.

Figure 7:
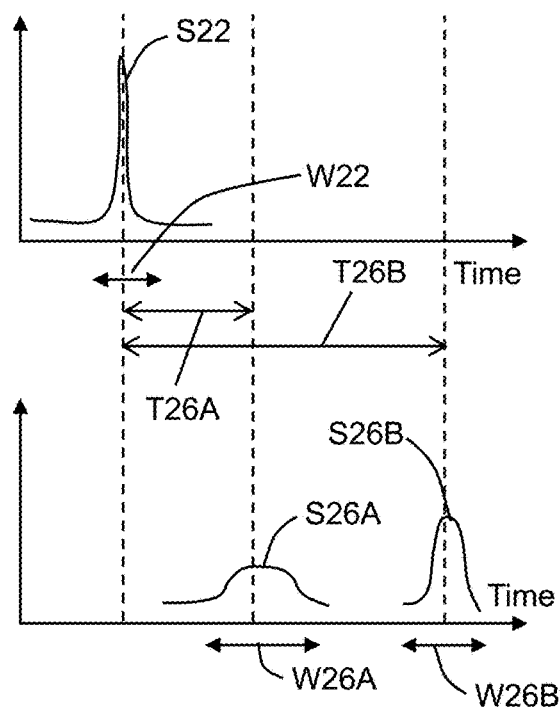
FIG. 7 illustrates a graphical representation of an impulse response signal indicative of the injection of nanoparticles injected at the injection site depicted in FIG. 6 and the spread of the signal in relation to the time delay in which some of the detectors positioned along the network of blood vessels in FIG. 6 detect the presence of the nanoparticles injected into the network according to an embodiment.

FIG. 7 illustrates a graphical representation of an impulse response signal S22 indicative of the injection of the nanoparticles 24 injected at the injection site 56 depicted in FIG. 6 and the spread of the input signal W22 in relation to the time delay T26A, T26B in which some of the detectors 26 (26A and 26B, respectively) positioned along the network 54 of blood vessels 14 in FIG. 6 detect the presence of the nanoparticles injected into the network according to an embodiment. As noted herein, the control unit 32 can include a timer that can record the time that the nanoparticle injector 22 injects the nanoparticles 24 into the blood flowing through the blood vessels 14. The timer can also record the time that the nanoparticle injector 22 stops injecting the nanoparticles into the blood and the time that each of the detectors 26 (e.g., 26A, 26B, 26C, 26D, 26E) detects the presence of the nanoparticles in the blood based on the emittance measurements obtained by the fluorescent meter 30 of each detector. In addition, the timer can record the shape of the impulse response signal S22 at the injection site 56 and the shape of the impulse response signal S26A, S26B at the time of detection by the detectors. The time delays T26A, T26B can be measured based on the time difference between the peak of the impulse response signal 22 in at the injection site 56 and the peak of the impulse response signal S26A, S26B, at each detector. In one embodiment, these impulse response signals recorded from the timer can take the form of a train of signals that are obtained from a source (e.g., the nanoparticle injector) and collected by one or more detectors.

FIG. 7 illustrates the time shift or delay that it takes the impulse response signal S22 to travel from the injection site 56 to the locations that the detectors 26A and 26B are positioned about the network 54 of blood vessels 14 and be detected. In addition, FIG. 7 shows how the shape of the impulse response signal S22 changes from the injection site 56 to the detection by detectors 26A and 26B. In particular, FIG. 7 shows that the impulse response signal S22 has a narrow spread W22 with a tall peak, in relation to the shape of the impulse response signal S26A at detector 26A which includes a wider spread W26A with a smaller peak, and the shape of the impulse response signal S26B at detector 26B which includes a spread W26B that is wider than the spread W22 obtained from the injection site 56 but narrower than the spread W26A obtained from the detector 26A, and a peak that is smaller than the peak of the impulse response signal S22 obtained from the injection site 56, but taller than the peak of the impulse response signal S26A obtained from the detector 26A. Generally, these differences can indicate the flow rate of the nanoparticles through the network of blood vessels and/or the sizes of blood vessels within the network. In particular, both the flow of blood and the blood vessel sizes affect all the parameters such as phase shift, the peak amplitude, and the impulse spread, of the injected nanoparticles.

In addition, control unit 32 can perform a fluorescence analysis on the data obtained from the nanoparticle injector 22 and the detectors 26 (e.g., 26A, 26B, 26C, 26D, 26E) to obtain various metric information. For example, the control unit 32 can determine the flow of the fluid 12. The control unit 32 can also determine the density of the nanoparticles 24 in the blood at the location that each detector is positioned about the network 54 of vessels 14. After making the above determinations, the control unit 32 can evaluate the flow rate and the data based thereon from the detectors 26 (e.g., 26A, 26B, 26C, 26D, 26E) with experimental data to ascertain an ability of the network of vessels 14 to transmit the blood.

FIG. 8 shows a schematic block diagram illustrating operation of the control unit 32 in a fluid flow evaluation system like the one depicted in FIG. 6 that includes a nanoparticle injector 22 that releases nanoparticles in a network of vessels and a plurality of detectors 26 (26A, 26B, . . . 26N) positioned about the network to detect the presence of the nanoparticles, that performs a fluorescent analysis that is used to obtain fluid and nanoparticle metrics according to embodiment. In particular, FIG. 8 schematically shows that the control unit 32 controls the operation of the nanoparticle injector 22 and the detectors 26 (26A, 26B, . . . 26N). This can include recording the time that the nanoparticle injector 22 injects nanoparticles into the network of vessels at an injection site, the time that the injector stops injecting the nanoparticles, and the time that each of the detectors senses the presence of the nanoparticles in the fluid (as provided by the corresponding detector or derived from data acquired from the detector). In addition, the schematic block diagram of FIG. 8 illustrates the data exchange relationship between the control unit 32 and the detectors 26 (26A, 26B, . . . 26N). This data exchange relationship between the control unit 32 and the detectors 26 can include, but is not limited to, one or more of: providing information pertaining to the detected fluorescence in the fluid, the location of the detected nanoparticles within the vessels, feedback on the operational settings of the radiation sources, the train of impulse response signals including signal height and spread, the size of the nanoparticles, and modification changes to be implemented by the detectors.

FIGS. 9A-9B show schematic views of fluid flow evaluation systems for evaluating a flow of biological fluid in a human body at different body positions and levels of activity according to an embodiment. In particular, FIG. 9A shows a fluid flow evaluation system 62 used with a human 60 in a bent body position in which the person is touching her toes. The fluid flow evaluation system 62 like others disclosed herein can include a nanoparticle injector 22 that can inject nanoparticles into a fluid flowing through a network of conduits at an injection site, and one or more detectors 26 located about the network of conduits to detect a presence of nanoparticles in the fluid at the location that the detectors are positioned. In one embodiment, the nanoparticle injector 22 of the fluid flow evaluation system 62 can inject nanoparticles into blood of the blood vessels that are part of the circulatory system of the human 60, while the detectors 26 can detect the presence of the particles in the blood vessels. Although FIG. 9A does not show a control unit, it is understood that this component can be used with the nanoparticle injector 22 and the detectors 26 to make various determinations which can include, but are not limited to, determining the blood flow, determining nanoparticle density, performing a fluorescence analysis, comparing results obtained from various positions of the human with experimental data obtained from those positions for the person 60, as well as other persons undergoing similar evaluations.

FIG. 9B shows a fluid flow evaluation system 64 that can be used to obtain biological fluid information from a human 60 during forms of exertion or physical stress. For example, the fluid flow evaluation system 64 can be used while the person 60 undergoes a stress test such as an exercise cardiogram to determine the presence of heart disease. As shown in FIG. 9B, the person 60 is walking or running on a treadmill 66 and is evaluated to see how his or her heart responds to the exercise. During this exercise cardiogram, electrical activity measurements obtained from a heart of the person via probes 68 can be monitored as can the blood pressure and pulse of the person through use of a blood pressure monitor 70. It is understood that other measurements can be obtained such as, but not limited to, temperature measurements and respiration measurements (e.g., oxygen levels).

In one embodiment, the fluid flow evaluation system 64 can operate in conjunction with the exercise cardiogram and the measurements obtained therefrom. For example, the fluid flow evaluation system 64, which can include the aforementioned components such as a nanoparticle injector 22, detectors 26 having radiation sources 28 and fluorescent meters 30, and a control unit 32, can obtain biological fluid flow information during the exercise cardiogram. In this manner, the control unit 32 can correlate biological fluid flow measurements such as blood flow with the other measurements (blood pressure, pulse, etc.) obtained during the exercise cardiogram. This can be useful in examining the flexibility of blood vessels during the exercise. It is understood that the exercise cardiogram is illustrative of only one possible stress test in which the fluid flow evaluation system 64 can be used, and those skilled in the art will appreciate that the system can be implemented with a variety of medical tests that a person or an animal can undergo for medical evaluation.

In general, the embodiments illustrated in FIGS. 9A-9B demonstrate a few scenarios in which the fluid evaluation systems described herein can be used in combination with various body positions, exertion tests, and the like, to ascertain how external factors can influence the flow of biological fluids within a living body. The examples described with regard to FIGS. 9A-9B represent only a few of the possible external factors that can influence the flow of biological fluids in a living body such as a human or an animal. Other factors that could be used with any of the various fluid flow evaluation systems to determine the effect on the flow of biological fluids can include, but are not limited to, proximity to meals, administration of drugs or gases, such as oxygen to a person under test, etc.

Having the capability to evaluate the flow of biological fluid in a living body at different body positions and different exercise levels as illustrated by the fluid flow evaluation systems 62, 64 of FIGS. 9A and 9B can be beneficial because it indicates the performance of the fluid channels within the body. For example, the flow of blood within the vessels can indicate the health of the blood vessels within the body, and changes in the flow during physical activity can indicate the vessel health. For instance, changes in the flow can indicate vessel flexibility and an ability to dilate during physical activity. By changing a person's body position, the fluid flow within the person is further influenced by gravity and various stresses on the body due to the changes. Observing fluid flow (such as blood flow to changes in body positions), while the person has a bent body position in which the person is touching his/her toes is only illustrative of various body positions that can be utilized. It is understood that those skilled in the art will appreciate that the system is applicable to other body positions that may be helpful in ascertaining information regarding the well-being of a living body such as a human or animal, e.g., information relating to the health of the blood vessels within the body.

Figure 10A:
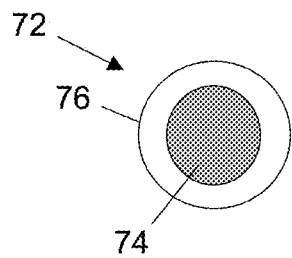
FIGS. 10A-10B show examples of different types of nanoparticles that can be used with the various embodiments of fluid flow evaluation systems described herein.
Figure 10B:
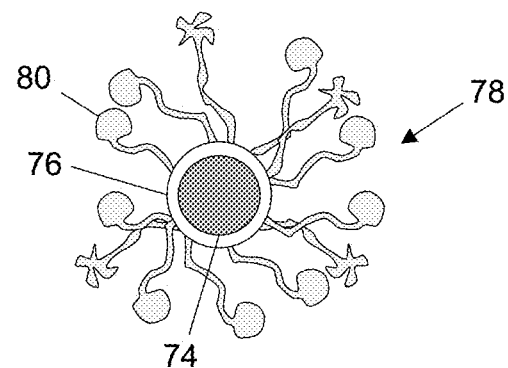

FIGS. 10A-10B show examples of different types of nanoparticles that can be used with the various embodiments of fluid flow evaluation systems described herein. The nanoparticles that are injected into the flow of the fluid in a conduit of any of the embodiments described herein can include a variety of different types of nanoparticles. In particular, the nanoparticles can vary by size, shape, and structure. For example, FIG. 10A shows a nanoparticle 72 that can include a magnetic core 74 and a fluorescent shell 76 enclosing the magnetic core. In one embodiment, the fluorescent shell 76 can have an emission of fluorescence in response to an external magnetic field applied thereto. A magnetic field probe is an example of a device that can be used to manipulate and sense the location of any nanoparticles that include a magnetic core 74 and a fluorescent shell 76 enclosing the magnetic core. In another example, a magnetic device, such as an electromagnetic solenoid, can apply a strong magnetic field that can be used to manipulate and sense these magnetic-based nanoparticles 72. As used herein, a strong magnetic field means a magnetic field sufficiently strong to affect the nanoparticles present in the fluid channels of the body. The magnetic field applied by the magnetic field probe, the magnetic device, or the like, can be time and/or space dependent. In an illustrative example, the magnetic field can be applied in vicinity of a cancer tumor at a time when the nanoparticles travel around the location of the tumor.

FIG. 10B shows a nanoparticle 78 with a magnetic core 74 and a fluorescent shell 76 enclosing the magnetic core having attachment features 80 extending from the shell that are configured to attach or bind with elements that may be present in a conduit. Examples of attachment features 80 can include, but are not limited to, organic molecules, such as proteins, that can bind to plaque present within the fluid channel. In a scenario in which the nanoparticles are injected into the biological fluid of a living body, the attachment features 80 can be used to bind with antibodies of cells that may be present within the conduits carrying the fluid. For example, in a scenario in which the nanoparticles are used with a fluid flow evaluation system to monitor the blood within the blood vessels of a living body, the attachment features 80 of the nanoparticle 78 can be used to bind with the antibodies that are typically present in the proximity of plaque buildup that is typically found within the blood vessels. In another example, the attachment features 80 of the nanoparticle 78 can be configured to bind to the antibodies that are typically present in the proximity of cancer cells. In an alternative scenario, the nanoparticles 78 can be molecules that contain medical compounds for affecting areas within the fluid channel.

Figure 11A:
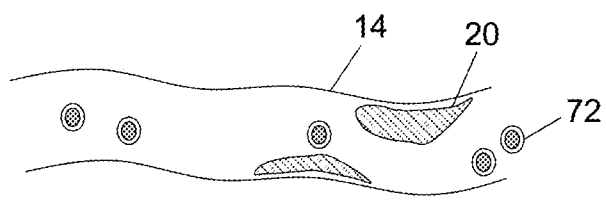
FIGS. 11A-11B show examples of the nanoparticles depicted in FIGS. 10A-10B, respectively, interacting with elements in the conduits in which the nanoparticles are flowing through according to embodiments.
Figure 11B:
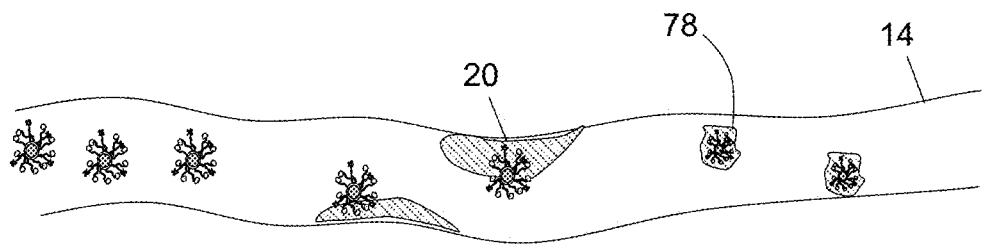

FIGS. 11A-11B show examples of the nanoparticles 72 and 78 depicted in FIGS. 10A-10B, respectively, interacting with elements in the conduits 14 in which the nanoparticles are flowing through according to embodiments. In the examples illustrated in FIGS. 11A-11B, the nanoparticles 72 and 78 are shown passing through vessels 14 such as arteries that have some plaque buildup 20. In this manner, the nanoparticles 72 and 78 can be altered by a magnetic field, or radiation for instances in which the particles do not contain a magnetic core 74 and a fluorescent shell 76, to have an interaction with the antibody cells around plaque buildup. This interaction can result in a chemical modification of the antibody cells around plaque buildup. This type of interaction is also possible in other embodiments in which the conduits are proximate cancerous cells. In either example, such modification can affect the fluorescence of the nanoparticles (e.g., reducing their fluorescence) which can be detected by a detector 26. As an example, this modification can appear as a reduction in the fluorescence of the nanoparticles 72, 78. The reduction of fluorescence can be used as additional information that describes the quality of the vessels (e.g., arteries, cells, etc.) of the living body.

Figure 12:
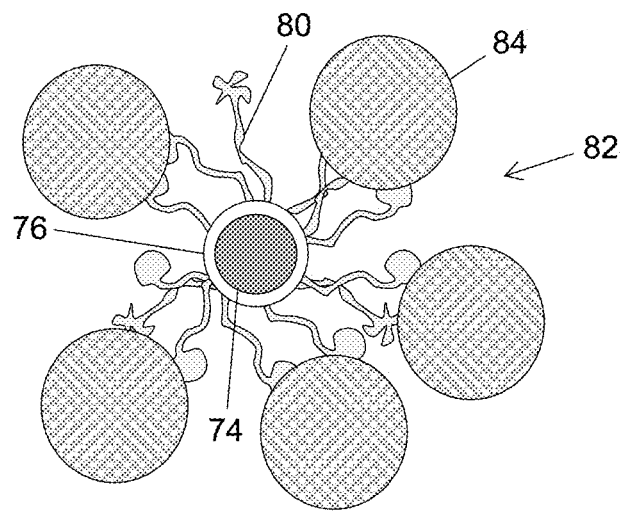
FIG. 12 shows a nanoparticle having medication attached thereto according to an embodiment.

FIG. 12 shows a nanoparticle 82 having medication 84 attached thereto according to an embodiment. In one embodiment, the nanoparticle 82 can include a magnetic core 74, a fluorescent shell 76 enclosing the magnetic core, attachment features 80 extending from the shell, and the medication 84 can adhere to the attachment features. The medication 84 can attach or adhere to the attachment features 80 of the nanoparticle 82 in one of a number approaches.

In this manner, the attachment features 80 of the nanoparticle 82 that attach or bind with elements that may be present in a conduit and the medicine 84 can be released for activation. To this extent, the medication 84 can be targeted for delivery to specific areas within a living body. In one example, the medication 84 can be targeted to attack cancer cells in a certain location of the body. In another example, the medication 84 can be used to reduce plaque buildup in the arteries of a person. It is understood that there are a multitude of other examples in which various forms of medication at varying dosages can be incorporated with the nanoparticles used in any of the embodiments described herein.

Figure 13:
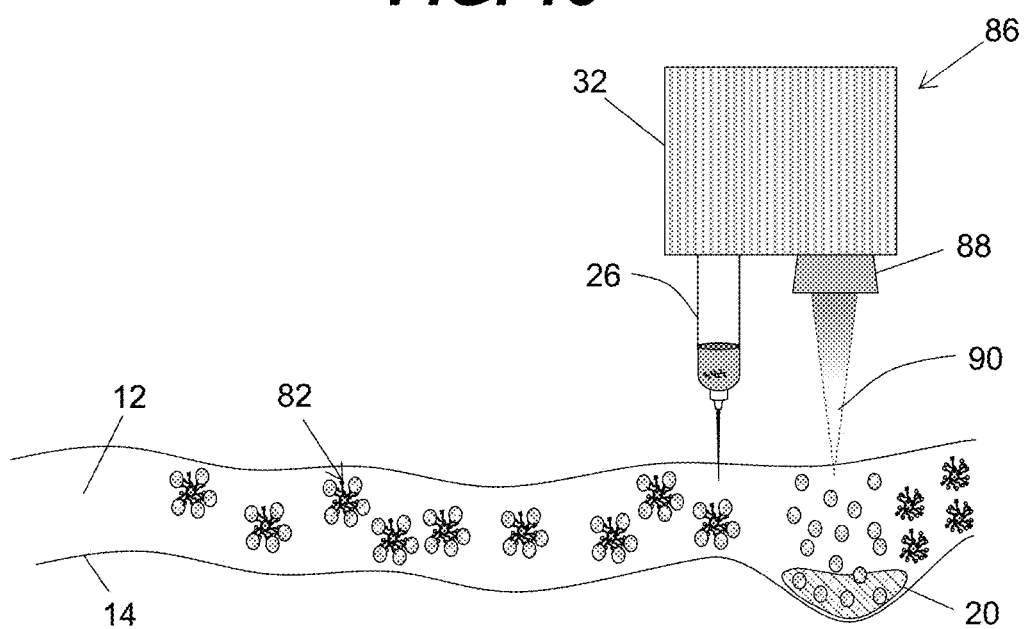
FIG. 13 shows a fluid flow evaluation system with nanoparticles having medication as depicted in FIG. 12 in a vessel of a human or an animal that is activated for release into the vessel with a medication activation device operating in conjunction with a detector according to an embodiment.

FIG. 13 shows a fluid flow evaluation system 86 having nanoparticles 82 with medication 84 attached thereto flowing through a conduit 14 such as a vessel within a human or animal that is activated for release by a medication activation device 88 operating in conjunction with a detector 26 according to an embodiment. Although not depicted in FIG. 13, the fluid flow evaluation system 86 can include a nanoparticle injector 22 configured to inject the plurality of nanoparticles 82 into the biological fluid 12 flowing through the vessel 14 at an injection site. The nanoparticles can each have medication 84 bound to the attachment features 80 as depicted in FIG. 12.

A detector 26 located about the vessel 14 can detect a presence of the nanoparticles 82 in a location that the detector is positioned about the vessels. As noted above, the detector 26 can include a fluid withdrawing device that is configured to withdraw a sample portion of the biological fluid 12 from the flow of the fluid at the location that the detector is positioned about the vessel 14. A radiation source can irradiate the biological fluid 12 withdrawn by the fluid withdrawing device with radiation. In one embodiment, the radiation source can include an ultraviolet radiation source that irradiates the biological fluid 12 with a target ultraviolet radiation.

The detector 26 can further include a fluorescent meter that is configured to sense a fluorescent signal emitted from the biological fluid irradiated with the radiation (e.g., ultraviolet radiation). The fluorescent signal is an indication that the nanoparticles 82 with the attached medication 84 are present at the location that the detector is positioned about the vessel 14. The fluorescent meter can note a time that the detector senses the presence of the nanoparticles 82 and medication 84 and a shape of an impulse response signal at the time of detection that is representative of the injection of the nanoparticles into the network of vessels that the vessel 14 is associated with.

The control unit 32 which is operatively coupled to the nanoparticle injector and the detector 26 can perform a fluorescent analysis of the biological fluid 12 in the conduit 14. The fluorescent analysis can include determining a flow rate of the biological fluid 12 through the vessel 14, and the density of the nanoparticles 82 in the fluid flow at the location that detector is positioned about the network of vessels.

The medication activation device 88 can operate in conjunction with the radiation source and the fluorescent meter components of the detector 26 and the control unit 32. In particular, the medication activation device 88 can activate a release of the medication 84 from the nanoparticles 82 in response to the fluorescent meter determining the presence of the nanoparticles in the fluid, and the results from the fluorescent analysis performed by the control unit 32. More specifically, the medication activation device can activate release of medication by physical (heating and magnetic field) and/or chemical means (injecting another medication that activates the medication 84) based on the fluorescent analysis. For instance, the medication activation device can be activated during observation of peak of fluorescence.

In one embodiment, the medication activation device 88 can include an infrared laser that is configured to irradiate the flow of nanoparticles 82 in the conduit 14 with infrared radiation 90. Irradiating the nanoparticles 82 with the infrared radiation 90 can cause an alteration that leads to a separation of the medication 84 from the nanoparticles 82. In another embodiment, the infrared radiation 90 can be configured to destroy the magnetic core 74 and fluorescent shell 76, leaving the medication 84 to remain in the vessel 14. In either example, the medication activation device 88 can be used to facilitate a targeted delivery of the medication 84 from the nanoparticles 82 to specific regions within a body. As noted above, there are a multitude of scenarios in which medication at varying dosages can be incorporated with the nanoparticles for targeted delivery to parts of a living body such as cancerous cells or to plaque buildup 20 as depicted in FIG. 13.

Although the medication activation device 88 is described as an infrared laser it is understood that this is only an example of one possibility for activating release of the medication from the nanoparticles. Those skilled in the art will appreciate that other devices and modalities can be used to release the medication 84 from the nanoparticles 82. Other examples of devices that can be used to activate the release of the medication 84 from the nanoparticles 82 can include, but are not limited to, infrared sources designed to heat the nanoparticles, the sources of magnetic fields, injectors of chemical compounds, and/or the like. In one embodiment, the medication activation device 88 such as an infrared laser, can be used in conjunction with an external magnetic field to attain a release of the medication 84 in certain a pattern and location within the conduit 14. For example, the magnetic field can be used to cluster the nanoparticles (e.g., those particles with a magnetic core and fluorescent shell) to certain points within the conduit 14. The magnetic field can be used to cluster the nanoparticles to these points prior to the release of the medication 84 by the infrared laser or during the release.

The fluid flow evaluation system 86 described in FIG. 13 illustrates one example in which nanoparticles with medication can be used to target a particular delivery of the medication to within a living body. However, it is understood that there are a multitude of possibilities for delivering medication through the use of nanoparticles injected into any of the network of conduits and vessels associated with a living body. For example, instead of using only one type of nanoparticle as illustrated in FIG. 13, it is possible to utilize several types of nanoparticles with each type having a different size, shape, structure, and/or medication attached thereto. In one embodiment, a first type of nanoparticle can contain a first medication and a second type of nanoparticle can contain the means for the releasing the first medication from the first type of nanoparticle. For example, the second type of nanoparticle can have a magnetic core that is configured to be altered and/or modified in response to an external magnetic field applied thereto. In one embodiment, the magnetic field can be used to congregate nanoparticles of the second type at a particular location. This collection of the nanoparticles of the second at specified location can facilitate the release of the medication from the nanoparticles of the first type through chemical interaction. In another embodiment, several types of different nanoparticles can be combined at a specific location within a vessel or conduit of a living body to facilitate a multitude of actions on the body. For example, a first set of nanoparticles can deliver the medicine to a specified location within the vessel, while the second set of nanoparticles can adhere to regions containing plaque.

Figure 14:
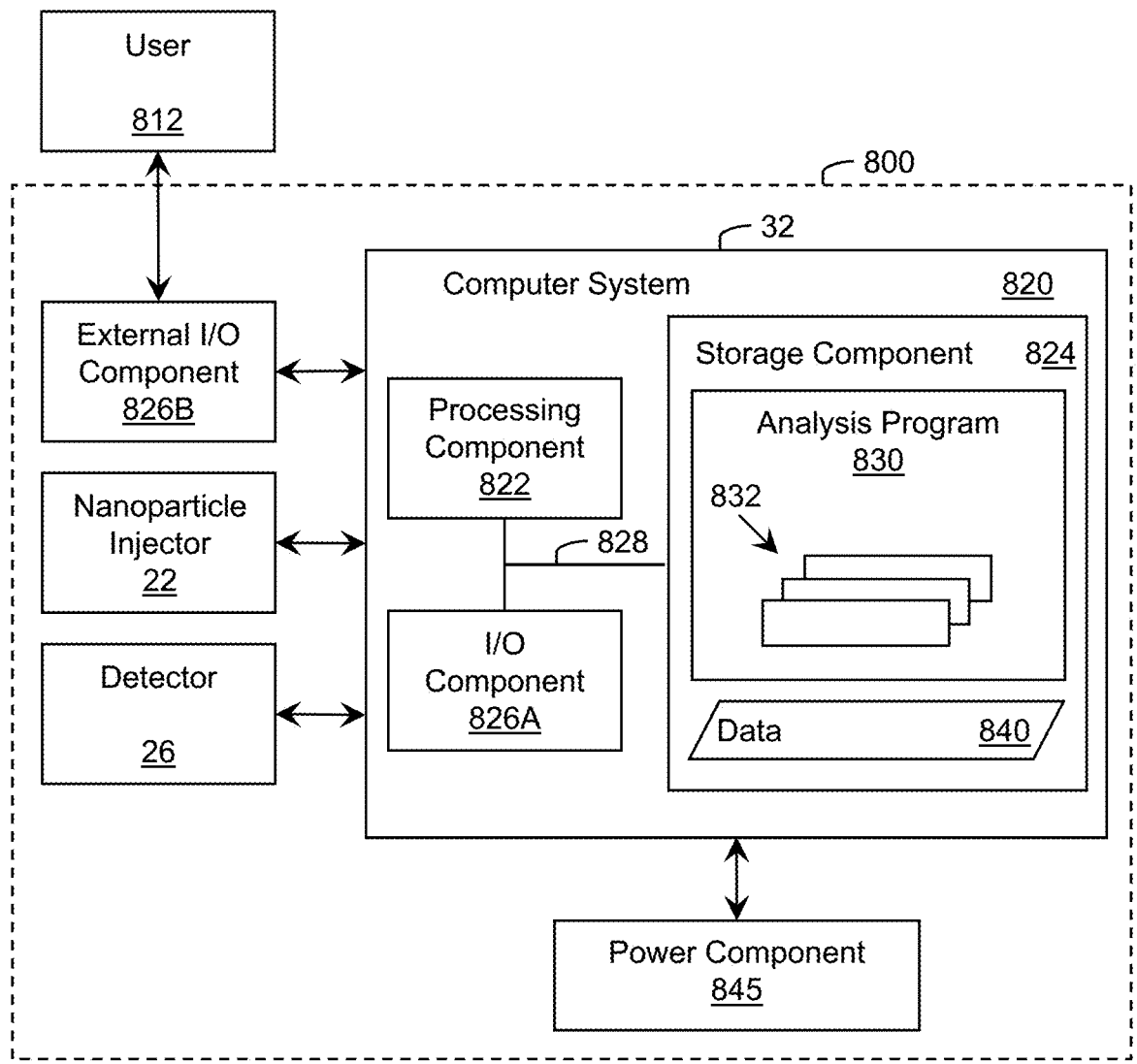
FIG. 14 shows a schematic block diagram representative of an overall processing architecture of a fluid flow evaluation system that is applicable to any of the systems described herein according to an embodiment.

FIG. 14 shows a schematic block diagram representative of an overall processing architecture of a fluid flow evaluation system 800 that is applicable to any of the systems described herein according to an embodiment. In this embodiment, the architecture 800 is shown including a nanoparticle injector 22 and a detector 26 for the purposes of illustrating the interaction of some of the components that are used to evaluate a fluid flowing in a conduit.

As depicted in FIG. 14 and described herein, the fluid flow evaluation system 800 can include a control unit 32. In one embodiment, the control unit 32 can be implemented as a computer system 820 including an analysis program 830, which makes the computer system 820 operable to manage operation of the detector(s) 26, the nanoparticle injector 22, and any other of the components that can be used in the manner described herein. In particular, the analysis program 830 can enable the computer system 820 to operate the components as described herein and process data corresponding to one or more attributes regarding the components, which can be stored as data 840. The computer system 820 can individually control each component and/or control two or more of the components as a group.

In an embodiment, during an initial period of operation, the computer system 820 can acquire data from at least one of the components regarding one or more attributes and generate data 840 for further processing. The computer system 820 can use the data 840 to control one or more aspects of the components.

Furthermore, one or more aspects of the operation of the components can be controlled or adjusted by a user 812 via an external interface I/O component 826B. The external interface I/O component 826B can include, for example, a touch screen that can selectively display user interface controls, such as control dials, which can enable the user 812 to adjust one or more of: an intensity, scheduling, and/or other operational properties of the nanoparticle injector 22 and/or detector 26 (e.g., operating parameters, radiation characteristics, etc.). In an embodiment, the external interface I/O component 826B could conceivably include a keyboard, a plurality of buttons, a joystick-like control mechanism, and/or the like, which can enable the user 812 to control one or more aspects of the operation of the detector 26 and/or the nanoparticle injector 22. The external interface I/O component 826B also can include any combination of various output devices (e.g., an LED, a visual display), which can be operated by the computer system 820 to provide status information pertaining to a fluid flow evaluation for use by the user 812. For example, the external interface I/O component 826B can include one or more LEDs for emitting a visual light for the user 812. In an embodiment, the external interface I/O component 826B can include a speaker for providing an alarm (e.g., an auditory signal).

The computer system 820 is shown including a processing component 822 (e.g., one or more processors), a storage component 824 (e.g., a storage hierarchy), an input/output (I/O) component 826A (e.g., one or more I/O interfaces and/or devices), and a communications pathway 828. In general, the processing component 822 executes program code, such as the analysis program 830, which is at least partially fixed in the storage component 824. While executing program code, the processing component 822 can process data, which can result in reading and/or writing transformed data from/to the storage component 824 and/or the I/O component 826A for further processing. The pathway 828 provides a communications link between each of the components in the computer system 820. The I/O component 826A and/or the external interface I/O component 826B can comprise one or more human I/O devices, which enable a human user 812 to interact with the computer system 820 and/or one or more communications devices to enable a system user 812 to communicate with the computer system 820 using any type of communications link. To this extent, during execution by the computer system 820, the analysis program 830 can manage a set of interfaces (e.g., graphical user interface(s), application program interface, and/or the like) that enable human and/or system users 812 to interact with the computer system 820. Furthermore, the analysis program 830 can enable the computer system 820 to manage (e.g., store, retrieve, create, manipulate, organize, present, etc.) the data, such as data 840, using any solution.

In any event, the computer system 820 can comprise one or more general purpose computing articles of manufacture (e.g., computing devices) capable of executing program code, such as the analysis program 830, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 830 can be embodied as any combination of system software and/or application software.

Furthermore, the analysis program 830 can be implemented using a set of modules 832. In this case, a module 832 can enable the computer system 820 to perform a set of tasks used by the analysis program 830, and can be separately developed and/or implemented apart from other portions of the analysis program 830. When the computer system 820 comprises multiple computing devices, each computing device can have only a portion of the analysis program 830 fixed thereon (e.g., one or more modules 832). However, it is understood that the computer system 820 and the analysis program 830 are only representative of various possible equivalent monitoring and/or control systems that may perform a process described herein with regard to the control unit, the ultraviolet radiation sources and the sensors. To this extent, in other embodiments, the functionality provided by the computer system 820 and the analysis program 830 can be at least partially be implemented by one or more computing devices that include any combination of general and/or specific purpose hardware with or without program code. In each embodiment, the hardware and program code, if included, can be created using standard engineering and programming techniques, respectively.

However, it is understood that the functionality described in conjunction therewith can be implemented by any type of control unit 32. For example, in another embodiment, the control unit 32 can be implemented without any computing device, e.g., using a closed loop circuit implementing a feedback control loop in which the outputs of one or more sensors are used as inputs to control the operation of the fluid flow evaluation system described herein.

Regardless, when the computer system 820 includes multiple computing devices, the computing devices can communicate over any type of communications link. Furthermore, while performing a process described herein, the computer system 820 can communicate with one or more other computer systems, such as the user 812, using any type of communications link. In either case, the communications link can comprise any combination of various types of wired and/or wireless links; comprise any combination of one or more types of networks; and/or utilize any combination of various types of transmission techniques and protocols.

All of the components depicted in FIG. 14 can receive power from a power component 845. The power component 845 can take the form of one or more batteries, a vibration power generator that can generate power based on magnetic inducted oscillations or stresses developed on a piezoelectric crystal, a wall plug for accessing electrical power supplied from a grid, and/or the like. In an embodiment, the power source can include a super capacitor that is rechargeable. Other power components that are suitable for use as the power component can include solar, a mechanical energy to electrical energy converter such as a piezoelectric crystal, a rechargeable device, etc.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system, comprising:
a detector configured to detect a binding between a set of nanoparticles flowing interspersed in a fluid and a set of biological elements in the fluid, wherein each nanoparticle includes a set of attachment features configured to bind each nanoparticle to each biological element, the detector including:
a radiation source configured to irradiate at least one portion of the fluid with radiation; and
a fluorescent meter configured to measure an amount of fluorescence emitted from the at least one portion of the fluid irradiated with the radiation; and a control unit configured to determine a set of attributes corresponding to the fluid as a function of the measured amount of fluorescence.

2. The system of claim 1, wherein the set of attributes includes a presence of the set of biological elements in the at least one portion of the fluid.

3. The system of claim 1, wherein the radiation source includes an ultraviolet radiation source, and wherein the control unit is further configured to control a plurality of operating parameters for the ultraviolet radiation source, including a wavelength of the radiation, an intensity of the radiation, a duration of the radiation, and/or the like.

4. The system of claim 1, wherein each nanoparticle in the set of nanoparticles comprises a magnetic core and a fluorescent shell enclosing the magnetic core, the fluorescent shell having an emission of fluorescence in response to the radiation emitted by the radiation source.

5. The system of claim 1, further comprising a nanoparticle injector configured to be inserted into the fluid to inject the set of nanoparticles into the fluid, wherein the fluid is a fluid of an organism and to be removed thereafter.

6. The system of claim 5, wherein the nanoparticle injector and the detector are located in close proximity to each other.

7. The system of claim 6, wherein the nanoparticle injector and the detector are integrated with each other as a monolithic unit, wherein the detector does not impede a flow of the fluid.

8. The system of claim 1, further comprising a waveguide configured to transport the radiation emitted from the radiation source to the fluid.

9. A system, comprising:
a detector configured to detect a binding between a set of nanoparticles flowing interspersed in a fluid and a set of biological elements in the fluid, the detector including:
an ultraviolet radiation source configured to irradiate at least one portion of the fluid with ultraviolet radiation; and a fluorescent meter configured to measure an amount of fluorescence emitted from the at least one portion of the fluid irradiated with the ultraviolet radiation; and
a control unit configured to determine a set of attributes corresponding to the fluid as a function of the measured amount of fluorescence.

10. The system of claim 9, wherein the set of attributes includes a presence of the biological elements in the at least one portion of the fluid.

11. The system of claim 9, wherein the control unit is further configured to control a plurality of operating parameters for the ultraviolet radiation source, including a wavelength of the radiation, an intensity of the radiation, a duration of the radiation, and/or the like.

12. The system of claim 9, wherein a wavelength range for the ultraviolet radiation is between 260 nanometers and 310 nanometers.

13. The system of claim 9, wherein each nanoparticle in the set of nanoparticles comprises a magnetic core and a fluorescent shell enclosing the magnetic core, the fluorescent shell having an emission of fluorescence in response to the ultraviolet radiation emitted by the ultraviolet radiation source.

14. The system of claim 9, further comprising a nanoparticle injector configured to be inserted into the fluid to inject the set of nanoparticles into the fluid, wherein the fluid is a fluid of an organism and to be removed thereafter, and wherein the nanoparticle injector and the detector are located in close proximity to each other.

15. The system of claim 14, wherein the nanoparticle injector and the detector are integrated with each other as a monolithic unit, wherein the detector does not impede a flow of the fluid.

16. The system of claim 9, further comprising a waveguide configured to transport the ultraviolet radiation emitted from the ultraviolet radiation source to the fluid.

17. A system, comprising:
a nanoparticle injector configured to be inserted into a fluid to inject a set of nanoparticles into an organism and to be removed thereafter, each nanoparticle having:
a set of attachment features configured to bind each nanoparticle to a biological element within the organism; and a fluorescent shell enclosing a magnetic core, the fluorescent shell having an emission of fluorescence in response to ultraviolet radiation;
a detector configured to detect a binding between the set of nanoparticles flowing interspersed in the fluid and a set of biological elements in the organism, the detector including:
an ultraviolet radiation source configured to irradiate at least one portion of the organism with ultraviolet radiation; and a fluorescent meter configured to measure an amount of fluorescence emitted from the at least one portion of fluid irradiated with the ultraviolet radiation; and
a control unit configured to determine a set of attributes corresponding to the organism as a function of the measured amount of fluorescence, the set of attributes including the presence of the nanoparticles in the fluid.

18. The system of claim 17, wherein a wavelength range for the ultraviolet radiation is between 260 nanometers and 310 nanometers.

19. The system of claim 17, wherein the nanoparticle injector and the detector are located in close proximity to each other, wherein the detector does not impede a flow of the fluid.

20. The system of claim 17, further comprising a waveguide configured to transport the ultraviolet radiation emitted from the ultraviolet radiation source to the organism.

* * * * *